United States Patent
Britto et al.

(10) Patent No.: US 11,945,838 B2
(45) Date of Patent: Apr. 2, 2024

(54) METHOD FOR SYNTHESIS OF PROTEIN AMPHIPHILES

(71) Applicant: INDIAN INSTITUTE OF SCIENCE EDUCATION AND RESEARCH, Pune (IN)

(72) Inventors: Sandanaraj Selvaraj Britto, Pune (IN); Mullapudi Mohan Reddy, Pune (IN)

(73) Assignee: INDIAN INSTITUTE OF SCIENCE EDUCATION AND RESEARCH, Pune (IN)

( * ) Notice: Subject to any disclaimer, the term of this patent is extended or adjusted under 35 U.S.C. 154(b) by 711 days.

(21) Appl. No.: 16/723,280

(22) Filed: Dec. 20, 2019

(65) Prior Publication Data
US 2020/0199175 A1    Jun. 25, 2020

(30) Foreign Application Priority Data
Dec. 20, 2018  (IN) ............................. 201821023023

(51) Int. Cl.
| | |
|---|---|
| A61K 47/54 | (2017.01) |
| A61K 38/17 | (2006.01) |
| A61K 38/38 | (2006.01) |
| A61K 38/47 | (2006.01) |
| A61K 38/48 | (2006.01) |
| A61K 47/60 | (2017.01) |
| C07D 401/14 | (2006.01) |
| C07D 403/12 | (2006.01) |
| C07K 1/18 | (2006.01) |

(52) U.S. Cl.
CPC ............ *C07K 1/18* (2013.01); *A61K 38/1767* (2013.01); *A61K 38/385* (2013.01); *A61K 38/47* (2013.01); *A61K 38/4826* (2013.01); *A61K 47/545* (2017.08); *A61K 47/60* (2017.08); *C07D 401/14* (2013.01); *C07D 403/12* (2013.01)

(58) Field of Classification Search
None
See application file for complete search history.

(56) References Cited

U.S. PATENT DOCUMENTS

| | | | |
|---|---|---|---|
| 2014/0322269 A1 | 10/2014 | Huang et al. | |
| 2017/0231260 A1 | 8/2017 | Britto | |

OTHER PUBLICATIONS

"Illustrated Glossary of Organic Chemistry", available online at http://www.chem.ucla.edu/~harding/IGOC/A/amphiphilic.html, 1 page (accessed on Oct. 12, 2022) (Year: 2022).*

"Hydrophilic", Biology Dictionary, available online at https://biologydictionary.net/hydrophilic/, 4 pages (2017) (Year: 2017).*
Dirks, "Preparation of biohybrid amphiphiles via the copper catalysed Huisgen [3 + 2] dipolar cycloaddition reaction{", Chem. Commun., 2005, 4172-4174, The Royal Society of Chemistry 2005.
Dong, et al., "Three-Dimensional Ordered Antibody Arrays Through Self-Assembly of Antibody-Polymer Conjugates", Angew. Chem. Int. Ed. 2017, 56, 1273-1277.
Heredia, et al., "In Situ Preparation of Protein-"Smart" Polymer Conjugates with Retention of Bioactivity", J. Am. Chem. Soc., 2005, 127, 16955-16960, published on the Web Nov. 10, 2005.
Kaba, et al., "Self-assembling protein nanoparticles with built-in flagellin domains increases protective efficacy of a Plasmodium falciparum based vaccine", Vaccine 36 (2018) 906-914, journal homepage: www.elsevier.com/ locate/vaccine.
Kalia, et al., "Exocyclic Olefinic Maleimides: Synthesis and Application for Stable and Thiol-Selective Bioconjugation", Angew. Chem. Int. Ed. 2016, 55, 1432-1435.
Kanekiyo, et al., "Self-assembling influenza nanoparticle vaccines elicit broadly neutralizing H1N1 antibodies", Nature, 104, vol. 499, Jul. 4, 2013.
Karch, et al., "The use of a *P. falciparum* specific coiled-coil domain to construct a self-assembling protein hanoparticle vaccine to prevent malaria", Journal of Nanobiotechnology (2017) 15:62, 10 pages.
Karch, et al., "Vaccine technologies: From whole organisms to rationally designed protein assemblies", Biochemical Pharmacology 120 (2016) 1-14, journal homepage: www.elsevier.com/locate/biochempharm.
Macdonald, et al., "O ne-step site-specific modification of native proteins with 2-pyridinecarboxyaldehydes", Nature Chemical Biology, vol. 11, May 2015, pp. 326-334.
Marcandalli, et al., "Induction of Potent Neutralizing Antibody Responses by a Designed Protein Nanoparticle Vaccine for Respiratory Syncytial Virus", Cell, 177, 1420-1431 Mar. 7, 2019.
Sandanaraj, et al., "Rational Design of Supramolecular Dynamic Protein Assemblies by Using a Micelle-Assisted Activity-Based Protein-Labeling Technology", Chem. Eur. J. 2018, 24, 16085-16096.
Velonia, et al., "Lipase Polystyrene Giant Amphiphiles", J. Am. Chem. Soc. 2002, 124, 4224-4225.
Kia, et al., "Site-Specific Conjugation of RAFT Polymers to Proteins via Expressed Protein Ligation", Chem. Comm. (Camb) Mar. 28, 2013, 49(25): 2566-2568 https://www.researchgate.net/publication/235669746.

* cited by examiner

*Primary Examiner* — Thea D'Ambrosio
(74) *Attorney, Agent, or Firm* — DeLizio, Peacock, Lewin & Guerra, ILLP

(57) ABSTRACT

The present invention discloses a novel cost effective method for synthesis of protein/peptide amphiphiles irrespective of functional and structural classification of proteins useful in designing a vaccine candidate from antigenic protein. The protein modification of the present invention is universal and hence any protein/peptide can be converted into amphiphilic proteins/peptides.

4 Claims, 8 Drawing Sheets

SCHEME 3

SCHEME 4

SCHEME 5

SCHEME 6

SCHEME 7

SCHEME 8

SCHEME 9

SCHEME 11

SCHEME 12

SCHEME 13

SCHEME 14

SCHEME 15

METHOD FOR SYNTHESIS OF PROTEIN AMPHIPHILES

FIELD OF INVENTION

The present invention relates to a novel cost effective method for synthesis of protein/peptide amphiphiles irrespective of functional and structural classification of proteins useful in designing a vaccine candidate from antigenic protein.

BACKGROUND AND PRIOR ART

Protein amphiphiles are made from globular hydrophilic proteins by attaching a lipid-like molecule. Until now, several methods are used to modify N-terminal amino acids directly or convert them into unique functional groups for further ligations. N-terminus-specific enzymatic ligation strategies are also emerging as powerful strategies. The most common site-selective protein modification using functionalization of N-terminal Amino Acids methods that are exploited are given below.
1. Selective modification of protein N termini using pH control.
2. Modification of specific amino acids at protein N termini.
3. Transamination of protein N termini, resulting in carbonyls that can be further reacted with alkoxyamines.
4. Immobilization of proteins through the N terminus.
5. Enzyme-mediated N-terminal protein modification
6. Enzyme-mediated N-terminal labeling to identify proteolytic cleavage sites.

While amine groups are abundant in proteins the "α-amine of the N terminus" stands out as a uniquely reactive site (shown in the table below). As a result, an increasing number of site-specific modification strategies are now targeting this position for applications in chemical and synthetic biology.

TABLE 1

| Amino acid | Avg Pka | Avg abundance |
| --- | --- | --- |
| Lysine | 10.5 | 5.9% |
| Cysteine | 8.0 | 1.9% |
| Aspartic acid | 3.5 | 5.3% |
| Glutamic acid | 4.0 | 6.3% |
| N-terminus | 6-8 | unique |

Chemical strategies that can target a single site on protein are rare but a versatile method for the one-step site selective modification of protein N termini, that does not require any genetic engineering of the protein target was reported recently. This reaction is demonstrated for 12 different proteins, including the soluble domain of the human estrogen receptor. The method is specific to the N terminus because of the increased availability of deprotonated α-amino groups and the required nucleophilic attack of the neighbouring amide nitrogen of the protein backbone on the initially formed N-terminal imine as shown below.

The method disclosed in the art though is compatible with the majority of proteins however cannot be applied to proteins that are N-terminally acylated. Also proteins with proline in the second position or those with N termini that are not exposed to solution (i.e. not available for reaction sterically) cannot be modified with this method.

The present inventors had earlier disclosed the method for synthesis of amphiphilic proteins from hydrophilic globular proteins which can be used to synthesize libraries of protein nanoparticle of different size, oligomeric state and surface charge. This was achieved using amphiphilic activity-based probes and micelle-assisted protein bioconjugation strategy. Efficient purification strategy for purification of amphiphilic protein was also disclosed by the present inventors. The methodology adopted was restricted to only enzyme family, serine proteases (about 200 proteins).

Accordingly, the US Patent Publication No. US2017231260 of the present inventors discloses a new amphiphilic protein scaffold named hydrophobin mimics comprising a protein head group, hydrophilic linker and hydrophobic tail and the process for the synthesis of a library of hydrophobin mimics thereof. The hydrophobin mimics of this invention self-assemble to form protein nanoparticles/nanocontainer either alone or in a specified chemical environment and find application in the area of bio-nanotechnology. This approach of creating protein amphiphiles is restricted only to enzymes.

The present inventors felt that the reported methods are very selective towards few classes of proteins or enzyme families and a need exists in the art to provide novel method applicable for synthesis of protein amphiphiles by site-specific modification of any protein useful for designing a vaccine candidate from antigenic protein.

An article titled "Design, display and immunogenicity of HIV1 gp120 fragment immunogens on virus-like particles" describe two strategies to display antigenic HIV1 gp120 fragments to the immune system, (i) by chimeric VLP display with Qβ particle and (ii) by chemical conjugation, to the surface of Qβ.2 (Marcandalli, J. et al. Induction of Potent Neutralizing Antibody Responses by a Designed Protein Nanoparticle Vaccine for Respiratory Syncytial Virus. Cell 176, 1420-1431. e1417 (2019)).

Another report describes the structure-based design of a self-assembling two-component protein nanoparticle vaccine for the respiratory syncytial virus. This particle presents a prefusion-stabilized variant of the F glycoprotein trimer (DS-Cav1) in an ordered, repetitive array on the particle exterior at controllable density.

To summarize the vaccine literature the prior art uses techniques like (i) Conjugation with another particle or (ii) Co-expression with viruses or (iii) Fusion with particle-forming proteins.

An article titled "Three-dimensional ordered antibody arrays through self-assembly of antibody-polymer conjugates" describes a method to make well-defined, full-length antibody-polymer conjugates (APCs) by a two-step sequential click approach with a combination of oxime ligation and strain promoted alkyne-azide cycloaddition. These APCs were able to self-assemble into lamellar nanostructures with alternating IgG and poly(N-isopropylacrylamide) (PNIPAM) nanodomains.

In order to increase the repertoire of synthetic amphiphilic proteins/peptides, it is one of the objectives of the present invention to provide novel method for synthesis of protein/peptide amphiphiles by site-specific modification of N-terminus or free thiol residue (native or introduced at any position) of any protein/peptide.

The other objective of the present invention is to create a protein complex with required dimensions from self-assembled protein/peptide amphiphiles.

SUMMARY OF THE INVENTION

In lieu with the above, the present invention provides a cost effective process for synthesis of protein/peptide amphiphiles irrespective of functional and structural classification of proteins.

In an aspect, any protein/peptide is converted into amphiphilic proteins/peptides by site-specific modification of the active sites such as N-terminus protein/peptide, free thiol residues (native or introduced) of the protein/peptide and such active sites of any protein/peptide by method of the present invention.

Accordingly, the present invention provides a cost effective process for synthesis of protein/peptide amphiphiles irrespective of functional and structural classification of proteins of general Formula (I), depicted in FIG. 1. The process includes:
  i. Functionalizing the hydrophilic spacer to obtain functionalized active amphiphilic probe (AAP), and
  ii. Conjugating said functionalized amphiphilic activity probe (AAP) of step (i) to reactive sites of proteins/peptides through micelle assisted protein labelling to yield the desired product . . . and self-assembling the conjugated protein/peptides.

In an aspect of the present invention, the functionalization of the hydrophilic spacer is carried out with groups selected from 2-pyridine carboxaldehyde or maleimide that can conjugate with the N-terminus or free thiol residues (native or introduced), of any protein/peptide.

In another aspect, the present invention provides synthesis of functionalized active amphiphilic probe (AAP) comprising;
  i. Reacting the tosylate compound (6) with piperazine to obtain compound (7);
  ii. Reacting compound (7) with tosylated 2-pyridine carboxaldehyde (3) in presence of base to obtain functionalized 2-PCA (pyridine carboxaldehyde) active amphiphilic probe (8);
  OR
  iii. Azidating the tosylate compound (6) to obtain azido compound (9) followed by reduction to amine (10);
  iv. Reacting amine (10) with N-(methoxy carbonyl) maleimide in presence of base to obtain maleimide functionalized active amphiphilic probe (11).

In another aspect, the present invention provides process for preparation of protein/peptide amphiphiles by site-specific modification of N-terminus comprising;
  i. Reacting the tosylate compound (6) with piperazine to obtain compound (7);
  ii. Reacting compound (7) with tosylated 2-pyridine carboxaldehyde (3) in presence of base to obtain functionalized 2-PCA (pyridine carboxaldehyde) active amphiphilic probe (8); and
  iii. Micelle assisted protein labelling of N-terminus with functionalized 2-PCA (pyridine carboxaldehyde) active amphiphilic probe (8) of step (ii) followed by purification.

In yet another aspect, the present invention provides process for preparation of protein/peptide amphiphiles by site-specific modification of cysteine comprising;
  i. Azidating the tosylate compound (6) to obtain azido compound (9) followed by reduction to amine (10);
  ii. Reacting amine (10) with N-(methoxy carbonyl) maleimide in presence of base to obtain maleimide functionalized active amphiphilic probe (11); and
  iii. Micelle assisted protein labelling of cysteine/free thiol residue (native or introduced) with maleimide functionalized active amphiphilic probe (11) of step (ii) followed by purification.

In an aspect, the tosylated 2-pyridine carboxaldehyde (3) was prepared by oxidation of 2,6-pyridinedimethanol (1) with suitable oxidizing agent such as selenium dioxide in presence of solvent to obtain compound (2) which was further treated with tosyl chloride to yield tosylated 2-pyridine carboxaldehyde (3).

In another aspect, the tosylated compound (6) was prepared by reacting tosylated alkyne terminated oligo ethylene glycol (4) with azide compound (5) in presence CuSO4 and sodium ascorbate as per our earlier protocol[3] The alkyne terminated oligo ethylene glycol (4) and the azide compound (5) are prepared by the process described in our earlier protocol[3].

The base for the process is selected from organic base or inorganic base which includes but is not limited to ethylamine, triethylamine, pyridine, piperazine, alkali/alkaline metal carbonates and bicarbonates and the like. The solvent for the synthesis is selected from polar or non-polar, protic or aprotic solvents which include but is not limited to alcohols, ethers, ketones, nitriles, esters, halogenated hydrocarbons and the like.

In another preferred aspect, the present invention provides site-modified protein/peptide amphiphiles of general Formula (I), depicted in FIG. 1. The amphiphiles of general Formula (I) include:

A modified protein, which may be selected from bovine serum albumin (BSA), green fluorescent protein (GFP), Lysozyme and the like; Proteases selected from serine, cysteine, aspartic and metalloproteases like trypsin, chymotrypsin, and subtilisin and the like; Fusion proteins and/or genetically edited proteins comprising of serine protease and other functional or therapeutic proteins, antibody, peptide, and the like;

A functionalized hydrophilic spacer group, which may be selected from Oligo ethylene glycol derivative that can react with N-terminus of protein or cysteine/free thiol residue (native or introduced at any position) wherein the functional group is selected from 2-pyridine carboxaldehyde (2-PCA) or maleimide group; and A hydrophobic tail comprising of benzyl ether dendrimers with varying alkyl chains.

In another preferred aspect, the present invention provides site-modified protein/peptide amphiphiles of general Formula (Ia):

$$MP\text{-}SG\text{-}HT \qquad \text{(Ia)}$$

where MP is a modified protein; SG is a functionalized hydrophilic spacer group; and HT is a hydrophilic tail. In the amphiphiles of general Formula (Ia), The modified protein MP may be selected from bovine serum albumin (BSA), green fluorescent protein (GFP), Lysozyme and the like; Proteases selected from serine, cysteine, aspartic and metalloproteases like trypsin, chymotrypsin, and subtilisin and the like; Fusion proteins and/or genetically edited proteins comprising of serine protease and other functional or therapeutic proteins, antibody, peptide, and the like;

The functionalized hydrophilic spacer group SG, which may be selected from Oligo ethylene glycol derivative that can react with N-terminus of protein or cysteine/free thiol residue (native or introduced at any position) wherein the functional group is selected from 2-pyridine carboxaldehyde (2-PCA) or maleimide group; and The hydrophobic tail HT may be selected from benzyl ether dendrimers with varying alkyl chains.

In an aspect, the site modified protein/peptide amphiphiles of the present invention comprises;
i. BSA conjugated with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-1)methyl) picolinaldehydeamphibilic probe;
ii. Chymotrypsin conjugated with 2-pyridine carboxaldehyde functionalized 6-((4-(1-(1-(4-(octadecyloxy)benzyl)-1H-1,2,3-triazol-4-yl)-2, 5, 8, 11, 14, 17,20,23-octaoxapentacosan-25-yl)piperazin-1-yl)methyl)picolin aldehyde amphibilic probe;
iii. Lysozyme conjugated with 2-pyridine carboxaldehyde functionalized 6((4-(1-(1-(4-(octadecyloxy)benzyl)-1H-1,2,3-triazol-4-yl)-2, 5, 8, 11, 14, 17,20,23-octaoxapentacosan-25-yl)piperazin-1-yl)methyl) picolin aldehyde amphibilic probe;
iv. GPF conjugated with 2-pyridine carboxaldehyde functionalized 6((4-(1-(1-(4-(octadecyloxy)benzyl)-1H-1,2,3-triazol-4-yl)-2,5,8,11,14,17,20,23-octaoxapentacosan-25-yl)piperazin-1-yl) methyl) picolin aldehyde amphibilic probe
v. BSA conjugated with maleimide functionalized 1-(1-(1-(4-(octadecyloxy)benzyl)-1H-1,2,3-triazol-4-yl)-2,5,8,11,14,17,20,23-octaoxapentacosan-25-yl)-1H-pyrrole-2,5-dioneamphibilic probe;

In an aspect, the present invention provides a method that can convert any antigen into particle directly without the necessity of conjugation on another particle (Displaying) which can behave as a better immunogen and can find application in vaccine design.

DESCRIPTION OF FIGURES

FIG. 7 shows a process for protein modification of BSA-thiol with maleimide functionalized oligoethylene glycol terminated probe.

DETAILED DESCRIPTION OF THE INVENTION

The invention will now be described in its various preferred as well as optional embodiments, so that the various aspects therein will be more clearly understood and appreciated.

The present inventors had earlier disclosed the method for synthesis of amphiphilic proteins from hydrophilic globular proteins which can be used to synthesize libraries of protein complexes of different size, oligomeric state and surface charge. This was achieved using amphiphilic activity-based probes (AABPs) and Micelle-assisted protein bioconjugation strategy. The present inventors had also disclosed an efficient purification strategy for amphiphilic proteins. The methodology adopted was however restricted only to enzyme families like serine proteases (about 200 proteins). The present inventors felt that the reported methods are very selective towards few classes of proteins or enzyme families and a need exists in the art to provide a method which could be applicable for the synthesis of protein amphiphiles by site-specific modification of protein/peptide irrespective of its functional and structural classification.

Accordingly, the present invention discloses a cost effective novel method for synthesis of protein/peptide amphiphiles by site-specific modification of the reactive sites of proteins/peptides irrespective of its functional and structural classification.

Figure 1:
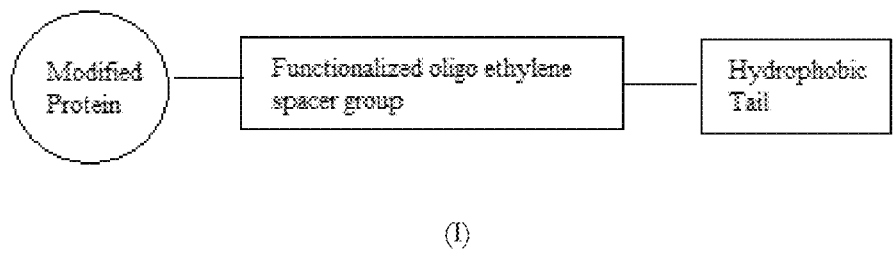
FIG. 1 shows the structure of a site-modified protein/peptide amphiphile of general Formula (I).

In an embodiment, the present invention relates to a cost effective process for synthesis of site-modified protein/peptide amphiphiles of formula (I), shown in FIG. 1, for any functional and structural proteins.

The process for synthesis of amphiphiles of formula (I) includes:
i. Functionalizing the oligoethylene hydrophilic spacer with 2-pyridine carboxaldehyde or maleimide to obtain functionalized active amphiphilic probe (AAP), and
ii. Conjugating said functionalized active amphiphilic probe (AAP) of step (i) to the N-terminus or free thiol residue (native or introduced at any position) of proteins/peptides and self-assembling the conjugated protein/peptides through micelle assisted protein labelling to yield the desired product.

The proteins/peptide of the present invention that can be modified with functionalized active amphipilic probe (AAP) is selected from bovine serum albumin (BSA), green fluorescent protein (GFP), Lysozyme and the like; Proteases selected from serine, cysteine, aspartic and metalloproteases like trypsin, chymotrypsin, and subtilisin and the like; Fusion proteins and/or genetically edited proteins comprising of serine protease and other functional or therapeutic proteins, antibody, peptide, and the like;

The hydrophilic spacer/linker warhead comprises a functionalized Oligo ethylene glycol derivative that can react with N-terminus of protein/peptide, cysteine/free thiol residue (native or introduced at any position) of protein/peptide wherein the functional group is selected from 2-pyridine carboxaldehyde (2-PCA) or thiol reactive maleimide group;

The hydrophobic tail linked to the hydrophilic spacer comprises benzyl ether dendrimers with varying alkyl chains that can self-assemble.

In another embodiment, the present invention discloses synthesis of functionalized active amphiphilic probe (AAP) which comprises;

i. Reacting the tosylate compound (6) with piperazine to obtain compound (7);
ii. Reacting compound (7) with tosylated 2-pyridine carboxaldehyde (3) in presence of base to obtain functionalized 2-PCA (pyridine carboxaldehyde) active amphiphilic probe (8);
OR
iii. azidating the tosylate compound (6) to obtain azido compound (9) followed by reduction to amine (10);
iv. reacting amine (10) with N-(methoxy carbonyl) maleimide in presence of base to obtain maleimide functionalized active amphiphilic probe (11).

The tosylated 2-pyridine carboxaldehyde (3) was prepared by oxidation of 2,6-pyridinedimethanol (1) with suitable oxidizing agent such as selenium dioxide in presence of solvent to obtain compound (2) which was further treated with tosyl chloride to yield tosylated 2-pyridine carboxaldehyde (3).

The base for the process is selected from organic base or inorganic base which includes but is not limited to ethylamine, triethylamine, pyridine, piperazine, alkali/alkaline metal carbonates and bicarbonates and the like. The solvent for the synthesis is selected from polar or non-polar, protic or aprotic solvents which include but is not limited to alcohols, ethers, ketones, nitriles, esters, halogenated hydrocarbons and the like.

In an embodiment, the process for preparing functionalized 2-PCA (pyridine carboxaldehyde) active amphiphilic probe (8) is depicted in Scheme 1 below:

about 65° C. for about 24 hours. The reaction mixture was cooled and diluted with dichloromethane. The mixture was filtered through celite, and the filtrate was concentrated under reduced pressure. The resulting crude material was purified by chromatography to get a liquid which became off-white solid later.

Tosyl chloride was added to the solution of alcohol in DCM at 0° C. TEA was then added to the above mixture, maintaining the temperature at 0° C. After about 1 hour at RT, the reaction mixture was concentrated and purified using column chromatography using hexane/ethyl acetate.

The tosylated alkyne terminated oligo ethylene glycol (4) and azide compound (5) was prepared by our previous protocol[3] were weighed in an oven dried RBF and THF was added, followed by water with vigorous stirring. Then, Na Ascorbate was added followed by $CuSO_4$ and allowed to react overnight. The reaction was extracted with DCM and concentrated under reduced pressure. The resulting crude tosylate compound (6) was purified by chromatography.

The tosylate compound (6) and piperzine were dissolved in THF and the mixture was refluxed for about 12 hours. The reaction mixture was then concentrated to obtain compound (7) and purified by column chromatography.

Compound (7), $K_2CO_3$ and tosylated 2-pyridine carboxaldehyde (3) were weighed in RBF. The mixture was dissolved in acetonitrile and refluxed at about 65° C. After about 16 hour, reaction mixture was concentrated and purified by column chromatography to obtain functionalized 2-PCA (pyridine carboxaldehyde) active amphiphilic probe (8).

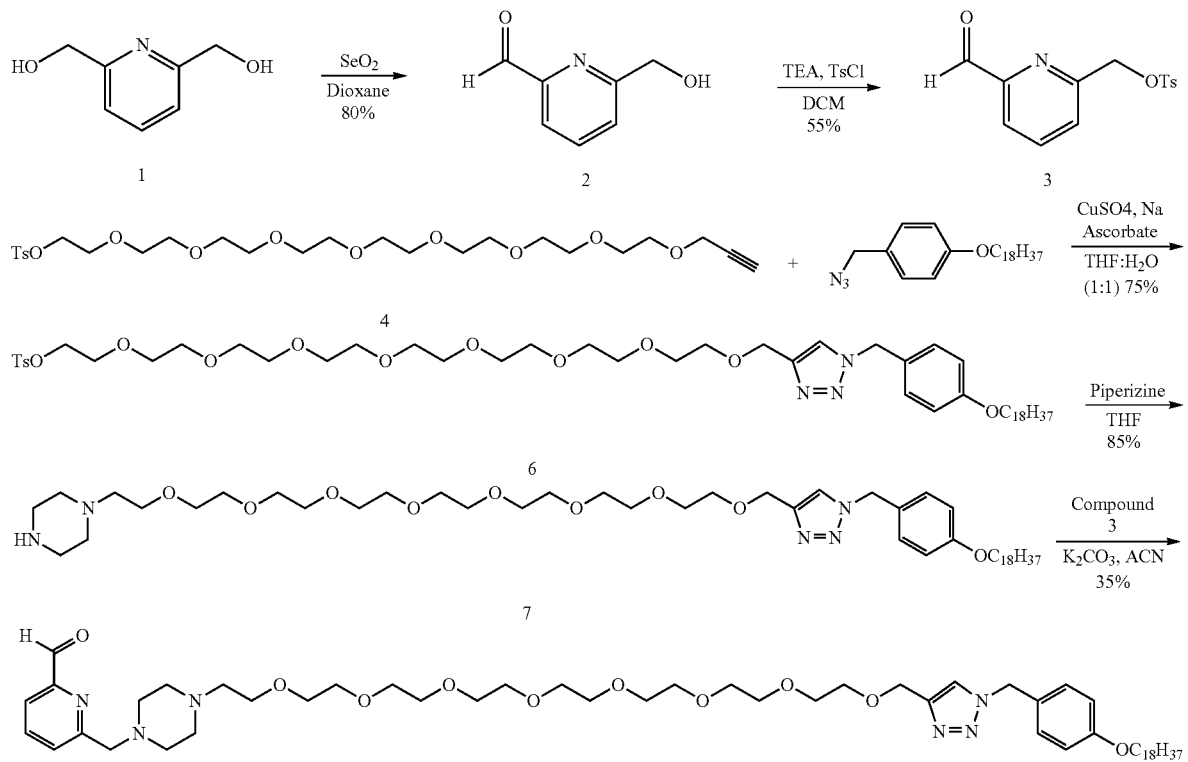

Accordingly, to a solution of 2,6-pyridinedimethanol (1) in 1,4-dioxane, selenium dioxide was added. The resulting mixture was sonicated for about 5 min and then stirred at In yet another embodiment, the process for preparing maleimide functionalized active amphiphilic probe (11) is depicted in Scheme 2 below:

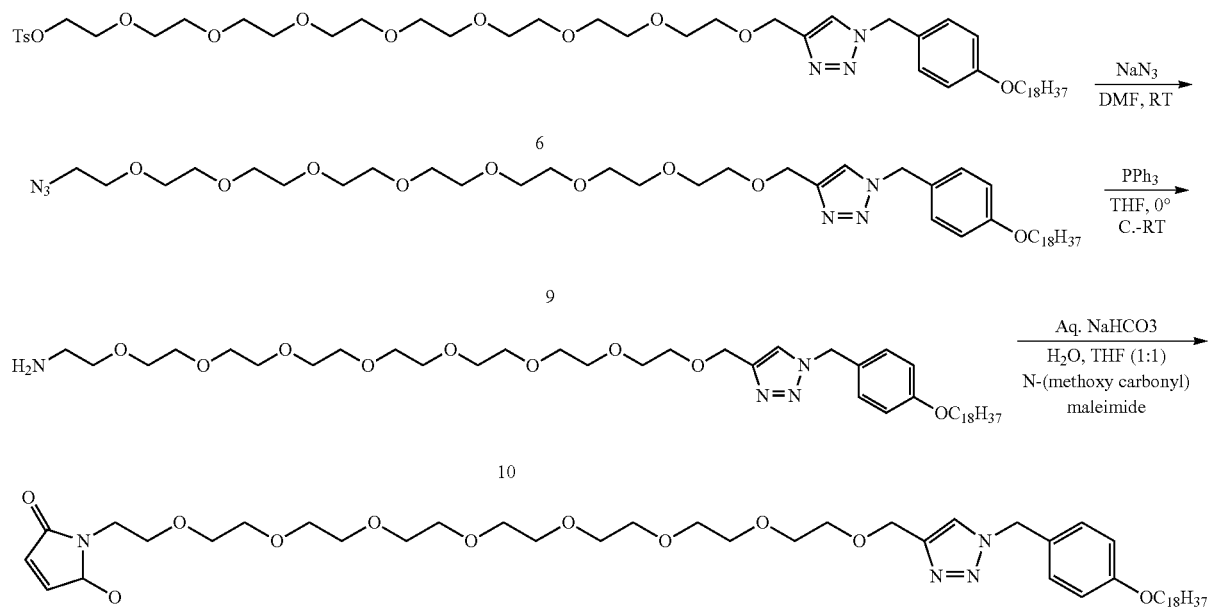

Accordingly, tosylate compound (6) was dissolved in DMF at RT. Sodium azide was then added to the reaction mixture and allowed to react at RT for 12 hour to obtain the azide (9). After this, the reaction mixture was concentrated and purified by column chromatography without any workup.

The above obtained azide (compound 9) was dissolved in THF at 0° C. and THF dissolved PPh₃, was further added at 0° C. The reaction mixture was allowed to react at RT to yield amine (10). Water was then added to the reaction mixture after 12 hours and allowed to stir for another 1 hour. The reaction mixture was extracted with DCM and purified using column chromatography.

The amine (10) was dissolved in a saturated aqueous solution of NaHCO₃ and cooled on an ice bath. This was followed by addition of N-(methoxy carbonyl) maleimide in portions under stirring. The mixture was stirred for about 1 hr at 0° C., followed by another 1 hr at room temperature. The maleimide functionalized activity probe (11) was extracted in solvent, dried, filtered concentrated and purified.

In an embodiment, the present invention relates to micelle assisted protein labelling comprising,
i. Preparing functionalized active amphiphilic probe (AAP) as shown above;
ii. Self-assembling the protein/peptide amphiphiles of Formula (I) obtained by coupling the pre-weighed protein with the active amphiphilic probes (AAP) homogenized in triton-X-100 at pH in the range 7.0-7.5, either alone or in high salt concentrations;
iii. Removing triton X-100 from the protein/peptide mixture using Ion exchange chromatography and eluting the native and protein/peptide amphiphiles using eluting buffer solution;
iv. Removing the native protein from the protein/peptide amphiphiles in high salt concentrations using size exclusion chromatography followed by desalting to obtain pure protein/peptide amphiphiles.

In another embodiment, the present invention discloses micelle assisted N-terminus protein labelling comprising;
i. Reacting the tosylate compound (6) with piperazine to obtain compound (7);
ii. Reacting compound (7) with tosylated 2-pyridine carboxaldehyde (3) in presence of base to obtain functionalized 2-PCA (pyridine carboxaldehyde) active amphiphilic probe (8);
iii. Self-assembling the protein/peptide amphiphiles of Formula (I) obtained by coupling the pre-weighed protein with the active amphiphilic probes (AAP) (8) homogenized in triton-X-100 at pH in the range 7.0-7.5, either alone or in high salt concentrations;
iv. Removing triton X-100 from the protein/peptide mixture using Ion exchange chromatography and eluting the native and protein/peptide amphiphiles using eluting buffer solution;
v. Removing the native protein from the protein/peptide amphiphiles in high salt concentrations using size exclusion chromatography followed by desalting to obtain pure protein/peptide amphiphiles.

Figure 2:
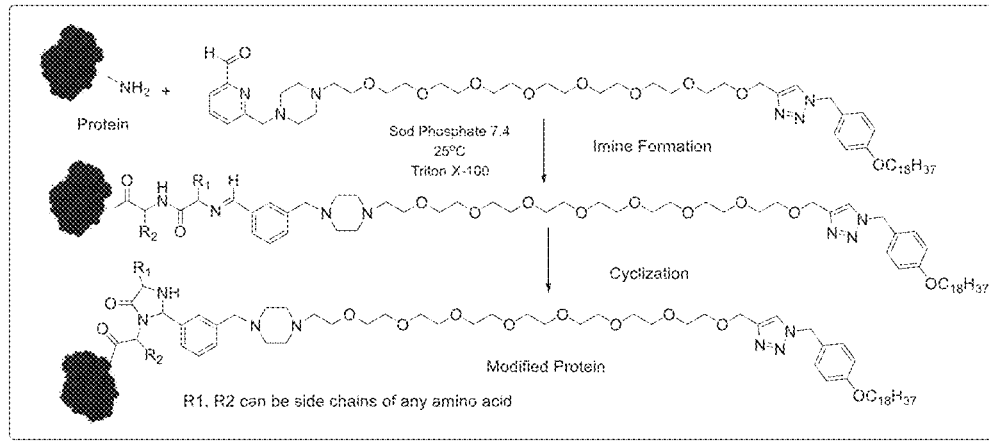
FIG. 2 shows a process for micelle assisted N-terminus protein labelling.

The process is depicted in Scheme 3, depicted in FIG. 2. In an embodiment the reactive 'alpha amine at the N-terminus' of the protein/peptide has pka value ranging from 6-8.

Accordingly, in the first step of protein modification, imine formation happens between the α-amino group at N-terminus and active amphiphilic probe (AAP). This is followed by the nucleophilic attack of the neighboring amide nitrogen on the initially formed N-terminal imine as shown above leading to the stable conjugate.

In yet another embodiment, the present invention discloses micelle assisted protein labelling at thiol group of cysteine (native or introduced) comprising;
i. Azidating the tosylate compound (6) to obtain azido compound (9) followed by reduction to amine (10);
ii. Reacting amine (10) with N-(methoxy carbonyl) maleimide in presence of base to obtain maleimide functionalized active amphiphilic probe (11);

iii. Self-assembling the protein/peptide amphiphiles of Formula (I) obtained by coupling the pre-weighed protein with the active amphiphilic probes (AAP) (11) homogenized in triton-X-100 at pH in the range 7.0-7.5, either alone or in high salt concentrations;

iv. Removing triton X-100 from the protein/peptide mixture using Ion exchange chromatography and eluting the native and protein/peptide amphiphiles using eluting buffer solution;

v. Removing the native protein from the protein/peptide amphiphiles in high salt concentrations using size exclusion chromatography followed by desalting to obtain pure protein/peptide amphiphiles.

Figure 3:
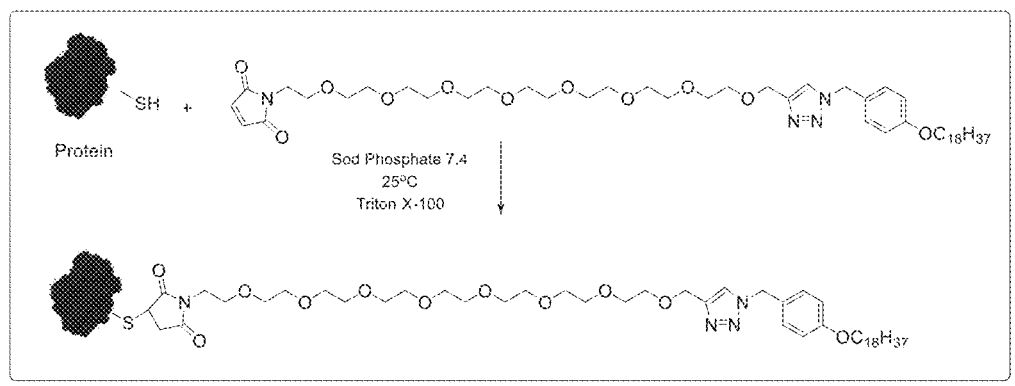
FIG. 3 shows a process for site-specific modification of cysteine.

The process for site-specific modification of cysteine is shown in Scheme 4, depicted in FIG. 3.

The present invention allows introduction of amphiphilicity and thereby self-assembling ability to proteins/peptides which is otherwise achieved in the art by complicated and costly genetic engineering.

Figure 4:
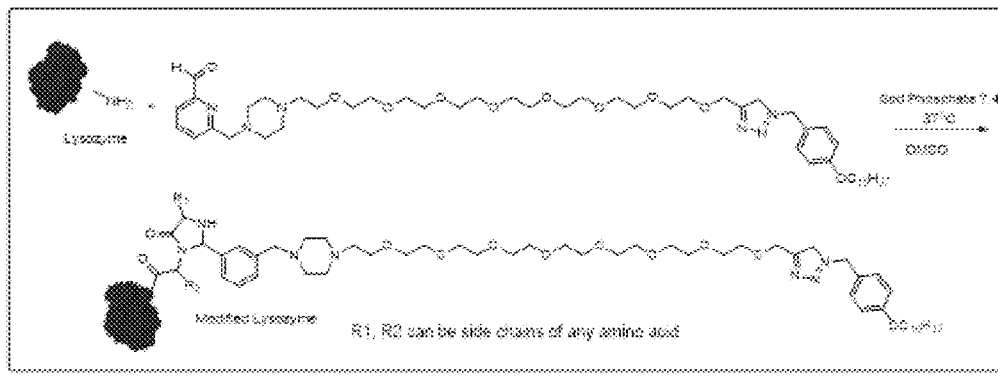
FIG. 4 shows a process for protein modification of N terminus of lysozyme with 2-PCA functionalized oligoethylene glycol terminated probe.

In another embodiment, the present invention discloses protein modification of N terminus of lysozyme with 2-PCA functionalized oligoethylene glycol terminated probe as shown in Scheme 5, depicted in FIG. 4.

Figure 5:
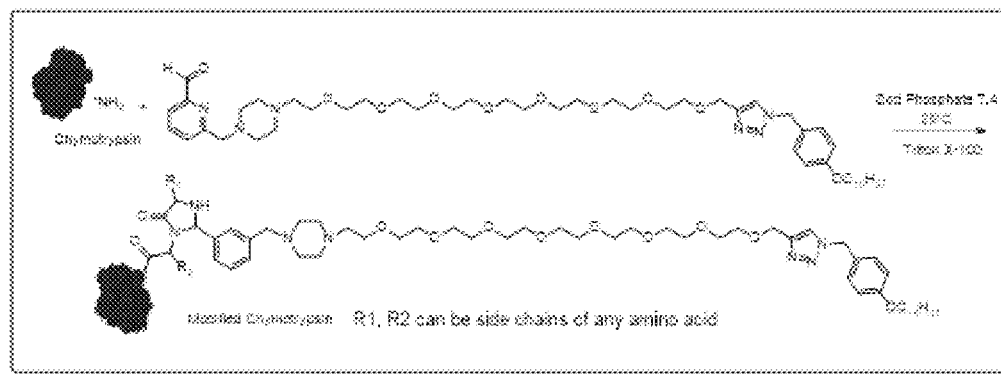
FIG. 5 shows a process for protein modification of N terminus of chymotrypsin with a 2-PCA functionalized oligoethylene glycol terminated probe.

In yet another embodiment, the present invention discloses protein modification of N terminus of chymotrypsin with 2-PCA functionalized oligoethylene glycol terminated probe as shown in Scheme 6, depicted in FIG. 5.

Figure 6:
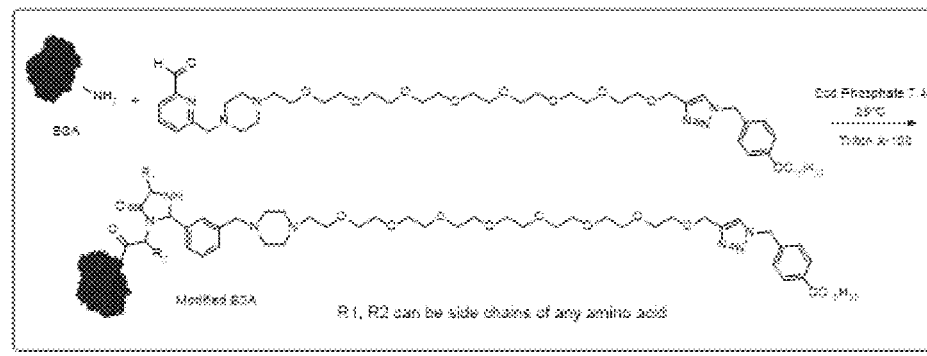
FIG. 6 shows a process for protein modification of N terminus of BSA with 2-PCA functinalized oligoethylene glycol terminated probe.

In yet another embodiment, the present invention discloses protein modification of N terminus of BSA with 2-PCA functionalized oligoethylene glycol terminated probe as shown in Scheme 7, depicted in FIG. 6.

Figure 7:
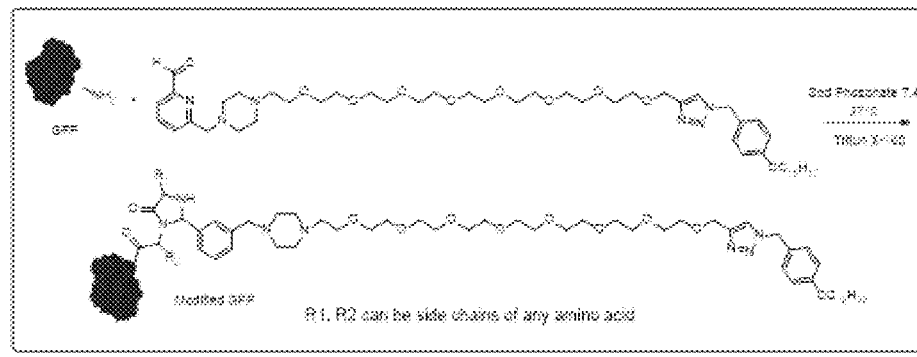
FIG. 7 shows a process for protein modification of N terminus of GFP with 2-PCA functinalized oligoethylene glycol terminated probe.

In another embodiment, the present invention discloses protein modification of N terminus of GFP with 2-PCA functionalized oligoethylene glycol terminated probe as shown in Scheme 8, depicted in FIG. 7.

Figure 8:
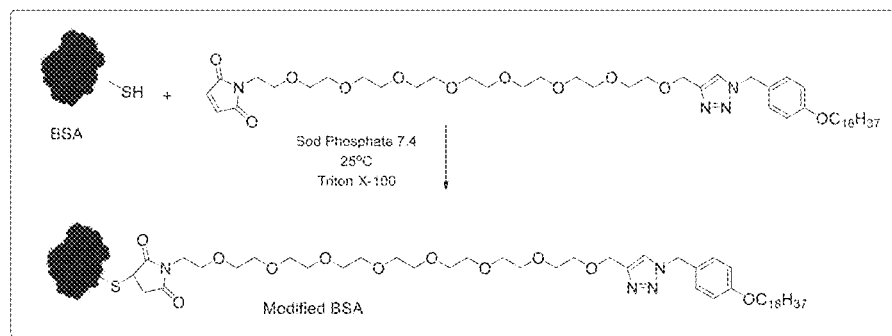

In yet another embodiment, the present invention discloses protein modification of BSA-thiol with maleimide functionalized oligoethylene glycol terminated probe as shown in Scheme 9, depicted in FIG. 8:

In another preferred embodiment, the present invention provides site-modified protein/peptide amphiphiles of general Formula (I), depicted in FIG. 1. The amphiphiles of general Formula (I) include a modified protein, a functionalized spacer group linked to the modified protein, and a hydrophobic tail linked to the functionalized spacer group.

The modified protein in Formula (I) may be a protein selected from bovine serum albumin (BSA), green fluorescent protein (GFP), Lysozyme and the like; a protease selected from serine, cysteine, aspartic and metalloproteases like trypsin, chymotrypsin, and subtilisin and the like; Fusion proteins and/or genetically edited proteins comprising of serine protease and other functional or therapeutic proteins, antibody, peptide, and the like.

The functionalized spacer group in Formula (I) may be selected from Oligo ethylene glycol derivatives that can react with the N-terminus of the modified protein, wherein the functional group is selected from 2-pyridine carboxaldehyde (2-PCA) or a thiol reactive maleimide group.

The hydrophobic tail linked to the functionalized spacer group in Formula (I) may be selected from benzyl ether dendrimers with varying alkyl chains.

In an embodiment, the site modified protein/peptide amphiphiles of the present invention comprises;

i. BSA conjugated with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-yl)methyl) picolin aldehyde amphibilic probe;

ii. Chymotrypsin conjugated with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-yl) methyl) picolin aldehyde amphibilic probe;

iii. Lysozyme conjugated with 2-pyridine carboxaldehyde functionalized 6((4-(1-(1-(4-(octadecyloxy)benzyl)-1H-1,2,3-triazol-4-yl)-2,5,8,11,14,17,20,23-octaoxapentacosan-25-yl)piperazin-1-yl)methyl)picolinaldehydeamphibilic probe;

iv. GPF conjugated with 2-pyridine carboxaldehyde functionalized 6((4-(1-(1-(4-(octadecyloxy)benzyl)-1H-1,2,3-triazol-4-yl)-2,5,8,11,14,17,20,23-octaoxapentacosan-25-yl)piperazin-1-yl) methyl) picolinaldehyde amphibilic probe v. BSA conjugated with maleimide functionalized 1-(1-(1-(4-(octadecyloxy)benzyl)-1H-1,2,3-triazol-4-yl)-2,5,8, 11,14,17,20,23-octaoxapentacosan-25-yl)-1H-pyrrole-2, 5-dioneamphibilic probe.

In another embodiment, the site specific modification applicable to universal proteins/peptides of the present invention is useful for biochemistry, pharmaceutical chemistry, and other fields.

In another embodiment, the present invention discloses a composition comprising the site modified protein/peptide amphiphile of Formula (I) along with acceptable excipients.

In another embodiment, the present invention discloses a strategy which can convert any protein/antigen into particle directly without the necessity of conjugation on another particle which makes protein/antigen a better immunogen that find application in vaccine design.

In an embodiment, the present invention discloses protein amphiphiles of Formula (I) to assemble into a particle of interest (creating a protein complex) with required dimensions in the range of 10-500 nm (as given in Table 1).

In another embodiment, the site modified protein amphiphiles of the present invention is useful in bio-nanotechnology, in drug delivery system, in vaccine development, for diagnostic and theranostics applications, as a spreading agent, surfactants, as tags to purify proteins from complex mixtures and as biosensors, to provide antibody-drug conjugate or as antimicrobial agents.

Experimental:

Protein Modification and Purification

Protein modification was carried out. In brief, triton X-100 was used to solubilize the active amphiphilic probe (AAP) at concentrations 100 times (20 mM) more than CMC or 2% of the total volume of the reaction mixture. Typically, for test reactions, the final volume of the reaction mixture was 1 mL. Proteins were weighed in microcentrifuge tubes and 500 µL 50 mM sodium phosphate pH 7.4 was added and mixed gently with a pipette to make 200 µM solutions. Then AAPs (50 to 100 equivalents) were weighed in a different microcentrifuge tube, followed by addition of 20 µL triton X-100 and 480 µL of 50 mM sodium phosphate pH 7.4 and vortexed for 15 minutes. When the AAP solution becomes clear, the protein solution was added into AAP solution to get 100 µM (1 mL) protein solutions and allowed to react for 24 h on rotospin at 10 rpm at 25° C. Protein modifications were carried out in falcon tubes at 200 mg scale following the linear scale-up of the procedure mentioned above for understanding the self-assembly behavior.

Maldi-TOF Monitoring of the Reaction Mixtures:

To monitor the extent of protein modification, the samples were directly withdrawn from the reaction mixture using a pipette and analyzed.

Purification of the Reaction Mixtures

All the protein conjugates were purified by two-step purification i.e. IEX and SEC, performed using Akta Pure. IEX was performed to remove triton X-100 using either SP separate or Q separate resins (GE) depending on isoelectric point (pI) and surface charges of proteins. Then SEC was performed to remove native proteins from the conjugates and the fractions containing conjugates were stored at −80° C.

Synthesis of the Amphiphilic Probe for Method 1 (N-Terminus Conjugation)

by chromatography using hexane/ethyl acetate to obtain the liquid which became off-white solid later.

Tosyl chloride was added to the solution of alcohol (2) in dichloromethane (DCM) at 0° C. Triethylamine (TEA) was then added to the above mixture, maintaining the temperature at 0° C. After 1 hour at RT, the reaction mixture was concentrated and purified using column chromatography using hexane/ethyl acetate.

Alkyne and azide were weighed in an oven dried RBF and THF was added, followed by water with vigorous stirring. Then, sodium ascorbate was added followed by $CuSO_4$ and allowed to react overnight. The reaction was extracted with DCM and then concentrated under reduced pressure. The resulting crude material was purified by chromatography using hexane/ethyl acetate.

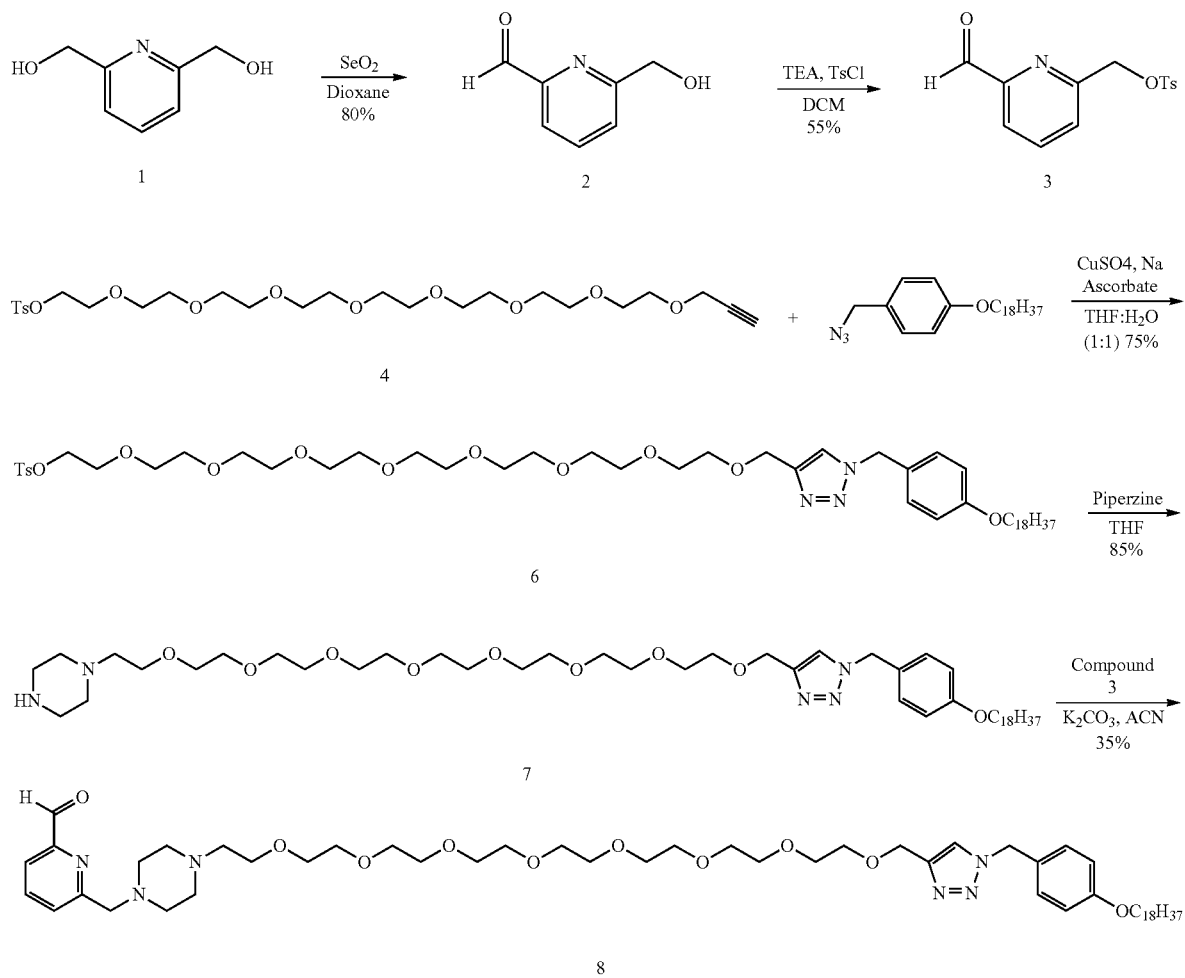

Synthesis of amphiphilic probe was done in three steps: 1. Synthesis of PCA derivative. 2. Synthesis of amphiphilic probe, 3. Synthesis of active amphiphilic probe.

To a solution of 2,6-pyridinedimethanol in 1,4-dioxane, selenium dioxide was added. The resulting mixture was sonicated for 5 min and then stirred at 65° C. for 24 hours. Then the reaction was cooled to room temperature and diluted with dichloromethane. The mixture was filtered through celite and the filtrate was concentrated under reduced pressure. The resulting crude material was purified Compound (6) (tosylate) and piperzine were dissolved in THF. Then the mixture was refluxed at 65° C. After 12 hour, reaction mixture was concentrated and purified by column chromatography.

Compound (7), $K_2CO_3$ and compound 3 (tosylate) were weighed in RBF. The mixture was then dissolved in acetonitrile (CAN) and refluxed at 65° C. After 16 hour, reaction mixture was concentrated and purified by column chromatography to obtain the final compound (8).

Synthesis of the Amphiphilic Probe for Method 2 (Thiol Conjugation)

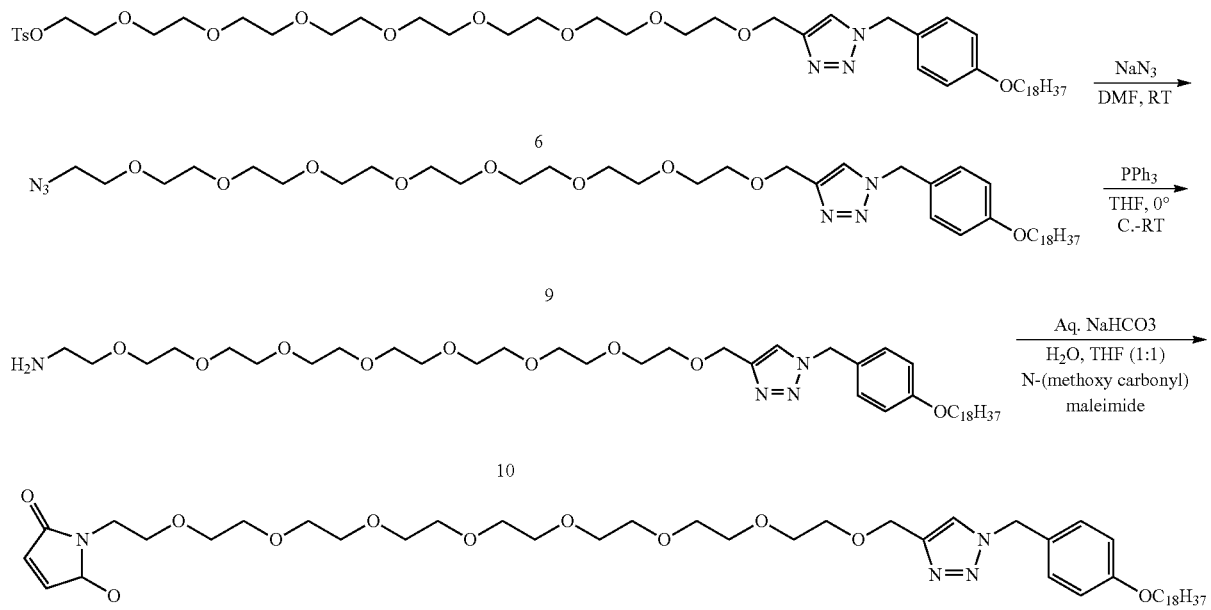

Synthesis of amphiphilic probe was done in three steps: i. Synthesis of azide derivative. b. Synthesis of amine, c. Synthesis of active amphiphilic probe with maleimide functionality.

Compound (6), the tosylate was dissolved in dimethyl formamide (DMF) at RT. Sodium azide was then added to the reaction mixture and allowed to react at RT for 12 hour. After this, the reaction mixture was concentrated and purified by column chromatography without any workup to obtain compound (9).

Above obtained azide (Compound 9) was dissolved in THF at 0° C. and THF dissolved PPh$_3$ and was added at 0° C. Then the reaction mixture was allowed to react at RT. Water was then added to the reaction mixture after 12 hours and allowed to stir for another 1 hour. The reaction mixture was extracted with DCM and purified using column chromatography to yield amine (10).

Amine (10) was dissolved in a saturated aqueous solution of NaHCO$_3$ and cooled on an ice bath. N-(methoxy carbonyl) maleimide was added in portions under stirring. The mixture was stirred for 1 hr at 0° C., followed by 1 hr at room temperature. After extraction with DCM, the organic phase was dried over anhydrous Na2SO4, filtered and concentrated. Purification by silica gel column chromatography (MeOH/DCM) yielded the product (11).

Synthesis of Individual Compounds
Compound 1: 6-(hydroxymethyl)picolinaldehyde

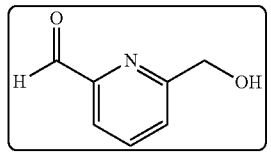

Mol. formula: $C_7H_7NO_2$
Mol. weight: 137.1380
Physical appearance: white solid
Yield: 60%

To a solution of 2,6-pyridinedimethanol (500 mg, 3.62 mmol) in 1,4-dioxane (10 mL), selenium dioxide (200 mg, 1.81 mmol) was added. The resulting mixture was sonicated for 5 min and then stirred at 65° C. for 24 hours. Then the reaction was cooled to room temperature and diluted with dichloromethane. The mixture was filtered through celite, and the filtrate was concentrated under reduced pressure. The resulting crude material was purified by chromatography using hexane/ethyl acetate to get a liquid which became off-white solid later (300 mg, 60%).

$^1$H NMR (400 MHz, CDCl$_3$): $\square_H$ 10.02 (s, 1H), 7.84 (m, 2H), 6.52 (m, 1H), 4.48 (s, 1H).

$^{13}$C NMR (100 MHz, CDCl$_3$): $\square_C$ 193.12, 160.43, 151.66, 137.86, 125.00, 120.65, 77.16, 64.24.

Compound 2: (6-formylpyridin-2-yl)methyl 4-methylbenzenesulfonate

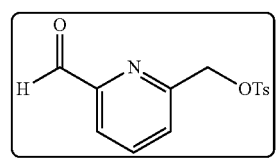

Mol. formula: $C_{14}H_{13}NO_4S$
Mol. weight: 291.3210
Physical appearance: white solid
Yield: 55%

Tosyl chloride (542 mg, 2.64 mmol) was added to the solution of alcohol (300 mg, 2.2 mmol) in DCM (10 mL) at 0° C. TEA (661 mg, 906 ul, 6.54 mmol) was then added to the above mixture, maintaining the temperature at 0° C. After 1 hour at RT, the reaction mixture was concentrated and purified using column chromatography using hexane/ethyl acetate (350 mg, 55%).

¹H NMR (400 MHz, CDCl₃): $\square_H$ 9.93 (s, 114), 7.85 (m, 4H), 7.66 (d, 1H), 7.35 (d, J=8.4, 2H), 5.22 (s, 2H), 2.43 (s, 31-1).
¹³C NMR (100 MHz, CDCl₃): $\square_C$ 154.80, 152.24, 145.41, 138.22, 132.67, 130.09, 128.18, 126.10, 121.35, 77.16, 71.19, 21.75.
HRMS (M+H): 292.0644.

Compound 6: 1-(1-(4-(octadecyloxy)benzyl)-1H-1,2,3-triazol-4-yl)-2,5,8,11,14,17,20,23-octaoxapentacosan-25-yl 4-methylbenzenesulfonate Synthesis of alkyne (compound 4) and azide (compound 5) was done.

Mol. formula: $C_{48}H_{87}N_5O_9$
Mol. weight: 878.2500
Physical appearance: yellow waxy solid
Yield: 82%

Compound 6 (tosylate) (2 g, 2.07 mmol) and piperzine (1.9 g, 22.09 mmol) were dissolved in THF (30 mL). Then the mixture was refluxed at 65° C. After 12 hour, reaction mixture was concentrated and purified by column chromatography (1.5 g, 82%).

¹H NMR (400 MHz, CDCl₃): $\square_H$ 7.48 (s, 1H), 7.12 (d, J=8.8, 2H), 6.77 (d, J=8.8, 2H), 5.43 (s, 2H), 4.53 (s, 2H),

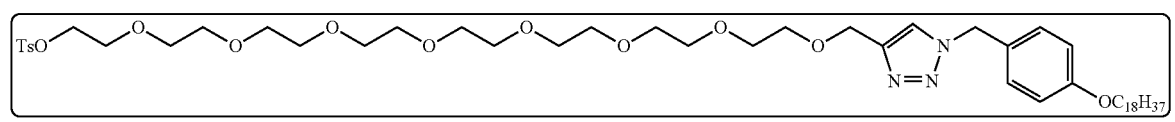

6

Mol. formula: $C_{51}H_{85}N_3O_{12}S$
Mol. weight: 964.3100
Physical appearance: yellow waxy solid
Yield: 75%

Alkyne (5 g, 8.89 mmol) and azide (2.82 g, 8.89 mmol) were weighed in an oven dried RBF and THF was added, followed by water with vigorous stirring. Then, Na Ascorbate (6.6 mg, 0.033 mmol) was added followed by CUSO₄ (2.6 mg, 0.016 mmol) and allowed to react overnight. The reaction was extracted with DCM and then concentrated 3.82 (t, J=6.4, 214), 3.51 (m, 31H), 3.04 (t, J=4.4, 4H), 2.51 (m, 5H), 1.66 (m, 2H), 1.34 (m, 3H), 1.15 (m, 31H), 0.769 (t, J=6.8, 3H).
¹³C NMR (100 MHz, CDCl₃): $\square_C$ 159.28, 145.12, 129.51, 126.20, 122.23, 114.77, 77.16, 70.36, 70.17, 69.50, 68.58, 68.34, 67.90, 64.47, 57.48, 57.17, 53.43, 50.12, 45.72, 43.55.
MALDI-TOF MS (M+Na): 900.72

Compound 8: 6-((4-(1-(1-(4-(octadecyloxy)benzyl)-1H-1,2,3-triazol-4-yl)-2,5,8,11,14,17,20,23-octaoxapentacosan-25-yl)piperazin-1-yl)methyl)picolinaldehyde

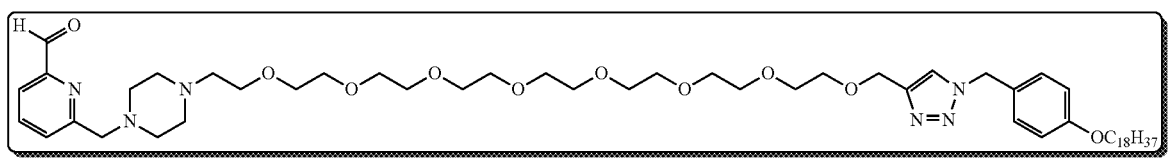

8 under reduced pressure. The resulting crude material was purified by chromatography using hexane/ethyl acetate (6.4 g, 75%).

¹H NMR (400 MHz, CDCl₃): $\square_H$ 7.78 (d, J=8.4, 2H), 7.47 (s, 1H), 7.33 (d, J=8, 2H), 7.20 (d, J=6.8, 2H), 6.86 (d, J=8, 2H), 5.41 (s, 2H), 4.62 (s, 2H), 4.1 (m, J=6.8, 2H), 3.92 (t, J=6.4, 2H), 3.63 (m, 30H), 3.5 (m, 5H), 1.75 (t, J=7.2, 2H), 1.42 (m, 2H), 1.24 (m, 34H), 0.86 (t, J=6.4, 3H).
¹³C NMR (100 MHz, CDCl₃): $\square_C$ 159.57, 144.89, 133.11, 129.79, 128.07, 126.37, 115.05, 77.16, 70.62, 69.78, 69.49, 68.75, 68.19, 32.01, 29.78, 29.69, 29.67, 29.48, 29.45, 29.28, 26.11, 22.78, 21.74, 14.23.
MALDI-TOF MS (M+Na): 986.55

Compound 7: 1-(1-(1-(4-(octadecyloxy)benzyl)-1H-1,2,3-triazol-4-yl)-2,5,8,11,14,17,20,23-octaoxapentacosan-25-yl)piperazine Mol. formula: $C_{55}H_{92}N_6O_{10}$
Mol. weight: 997.3730
Physical appearance: yellow waxy solid
Yield: 33%

Compound 7 (1.6 g, 1.82 mmol), K₂CO₃ (0.500 g, 3.62 mmol) and compound 3 (tosylate) (0.530 g, 1.82 mmol) were weighed in RBF. Then the mixture was dissolved in ACN (10 mL) and refluxed at 65° C. After 16 hour, reaction mixture was concentrated and purified by column chromatography (0.6 g, 33%).

¹H NMR (400 MHz, CDCl₃): $\square_H$ 10.06 (s, 1H), 7.83 (m, 2H), 7.8 (m, 1H), 7.43 (s, 1H), 7.21 (d, J=8.4, 2H), 7.67 (d, J=8.4, 2H), 5.42 (s, 2H), 4.63 (s, 2H), 3.92 (t, J=6.4, 2H), 3.75 (s, 2H), 3.61 (m, 32H), 2.59 (m, 9H), 1.75 (m, 2H), 1.42 (m, 2H), 1.24 (m, 3H), 0.86 (t, J=6.8, 3H).

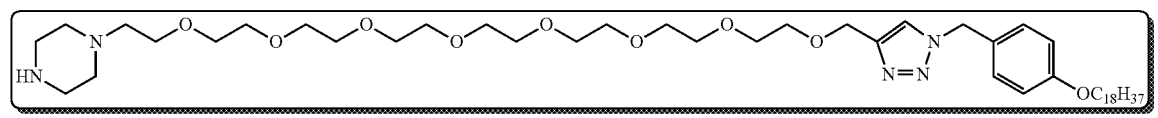

7

$^{13}$C NMR (100 MHz, CDCl$_3$): δ$_C$ 193.77, 137.51, 129.81, 120.29, 115.08, 77.16, 70.67, 70.48, 68.23, 64.91, 64.17, 57.80, 53.83, 53.68, 53.34, 32.04, 29.81, 29.61, 29.31, 26.14, 22.81, 14.25.

MALDI-TOF MS (M+Na): 1019.60.

Compound 9: 4-(25-azido-2,5,8,11,14,17,20,23-octaoxa-pentacosyl)-1-(4-(octadecyloxy)benzyl)-1H-1,2,3-triazole

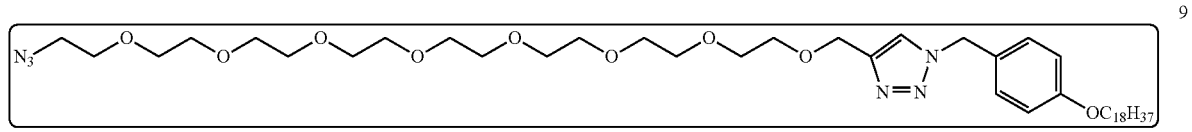

9

Mol. formula: C$_{44}$H$_{78}$N$_6$O$_9$
Mol. weight: 835.1410
Physical appearance: yellow waxy solid
Yield: 70%).

Tosylate (2 g, 2.0 mmol) was dissolved in DMF (10 mL) at RT. Then Sodium azide (0.674 g, 10.3 mmol) was added to the reaction mixture and allowed to react at RT for 12 hour. After this, the reaction mixture was concentrated and purified by column chromatography without any workup (1.2 g, 70%).

$^1$H NMR (400 MHz, CDCl$_3$): δ$_H$ 7.40 (s, 1H), 7.20 (d, J=8, 2H), 6.86 (d, J=8, 2H), 5.41 (s, 2H), 4.62 (s, 2H), 3.91 (t, J=6.8, 2H), 3.63 (m, 3214), 3.35 (t, J=4.8, 2H), 1.74 (t, J=6.8, 2H), 1.42 (m, 2H), 1.2 (m, 32H), 0.85 (t, J=6.4, 3H).

MALDI-TOF MS (M+Na): 874.58.

Compound 10: 1-(1-(4-(octadecyloxy)benzyl)-1H-1,2,3-triazol-4-yl)-2,5,8,11,14,17,20,23-octaoxapentacosan-25-amine

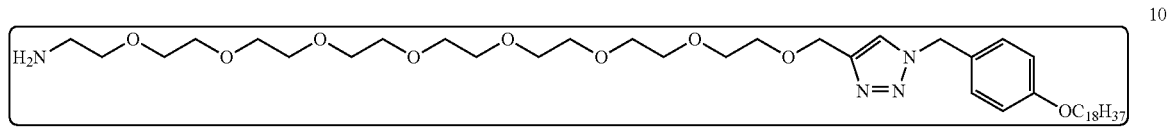

10

Mol. formula: C$_{44}$H$_{80}$N$_4$O$_9$
Mol. weight: 808.1430
Physical appearance: yellow waxy solid
Yield: 51%

Azide (Compound 9) (400 mg, 0.479 mmol) was dissolved in THF (7 mL) at 0° C. and THF (3 mL) dissolved PPh3 (250 mg, 0.954 mmol) and was added at 0° C. Then the reaction mixture was allowed to react at RT. Water was then added to the reaction mixture after 12 hours and allowed to stir for another 1 hour. Then the reaction mixture was extracted with DCM and purified using column chromatography (200 mg, 51%).

Compound 11: 1-(1-(1-(4-(octadecyloxy)benzyl)-1H-1,2,3-triazol-4-yl)-2,5,8,11,14,17,20,23-octaoxapentacosan-25-yl)-1H-pyrrole-2,5-dione

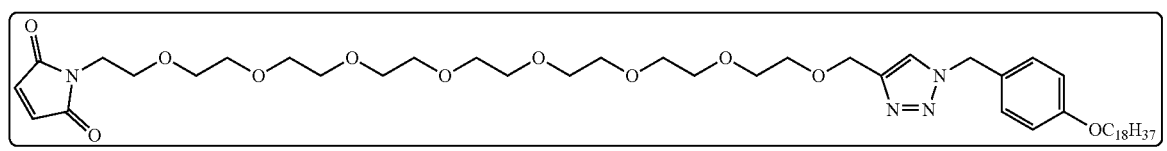

11

Mol. formula: $C_{48}H_{80}N_4O_{11}$
Mol. weight: 889.5824
Physical appearance: yellow waxy solid
Yield: 50%

Amine (100 mg, 0.123 mmol) was dissolved in a mixture of saturated aqueous solution of NaHCO3 (5 ml) and THF (5 ml) cooled on an ice bath. Then N-(methoxy carbonyl) maleimide (23 mg, 0.148 mmol) was added in portions over 5 min under vigorous stirring. The mixture was stirred for 1 hr at 0° C., followed by 1 hr at room temperature. After extraction with DCM, the organic phase was dried over anhydrous Na2SO4, filtered, and concentrated. Purification by silica gel column chromatography (MeOH/DCM) yielded the product as colorless oil after evaporation with DCM (55 mg, 50%).

$^1$H NMR (400 MHz, CDCl$_3$): $\delta_H$ 7.43 (s, 1H), 7.20 (d, J=8.8, 2H), 6.86 (d, J=8.8, 2H), 6.68 (s, 2H), 5.46 (s, 2H), 4.62 (s, 2H), 3.91 (t, J=6.1, 2H), 3.70 (t, J=5.6, 2H), 3.63 (m, 32H), 1.74 (m, 2H), 1.41 (m, 2H), 1.23 (m, 32H), 0.85 (t, J=7.2, 3H).

MALDI-TOF MS (M+Na): 911.58.

$^1$H NMR (400 MHz, CDCl$_3$): $\delta_H$ 7.40 (s, 1H), 7.20 (d, J=8.8, 2H), 6.86 (d, J=8.8, 2H), 5.43 (s, 2H), 4.64 (s, 2H), 3.93 (t, J=6.8, 2H), 3.68 (m, 32H), 3.38 (t, J=4.8, 2H), 1.76 (m, 2H), 1.42 (m, 2H), 1.33 (m, 30H), 0.87 (t, J=7.2, 3H).

MALDI-TOF MS (M+Na): 831.53.

Synthesis of alkyne terminated N-terminus probe

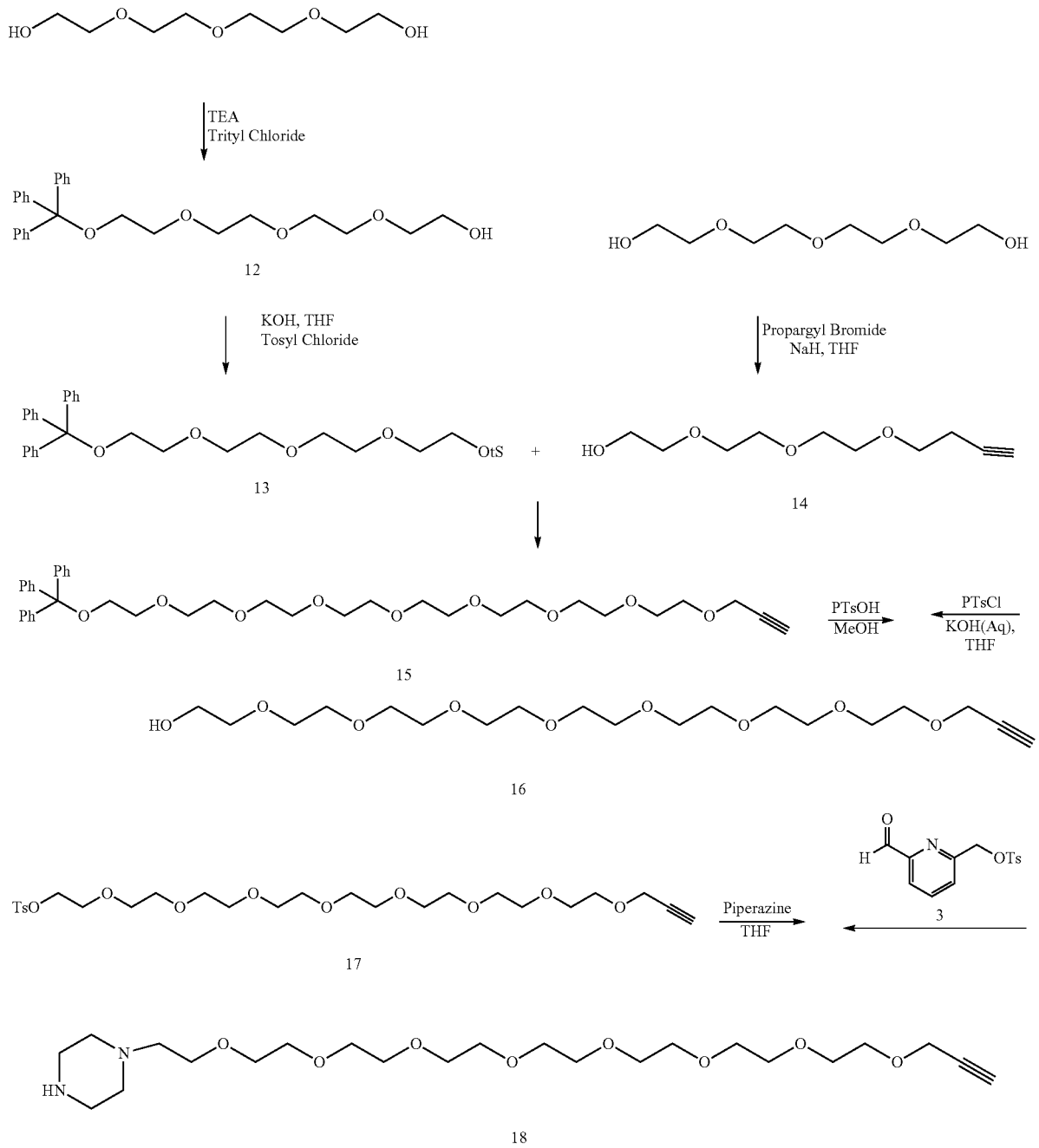

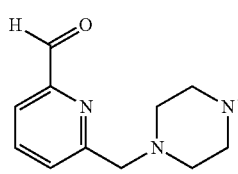

19

Compound 12: 1,1,1-triphenyl-2,5,8,11-tetraoxatridecan-13-ol

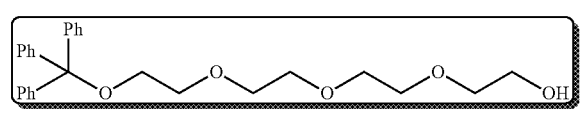

12

Mol. formula: $C_{27}H_{32}O_5$
Mol. weight: 436.5
Physical appearance: Colorless liquid
Yield: 85%

In an oven dried RBF, TEG (1 g) was dissolved with stirring in DCM at 0° C. TEA (0.134 g) was added to the flask in small portions immediately. After 15 minutes, tritylchloride (0.186 g) was added drop wise, maintaining the reaction at the same temperature. Then reaction was stirred for 24 hours at RT. Upon completion, aq NaHCO$_3$ was added drop wise. Resulting reaction mixture was extracted in DCM thrice. Combined organic layer was dried over Na$_2$SO$_4$ and concentrated under vacuum to get crude product which was purified using silica gel column chromatography.

Compound 13: 1,1,1-triphenyl-2,5,8,11-tetraoxatridecan-13-yl 4-methylbenzenesulfonate

13

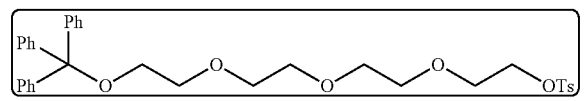

Mol. formula: $C_{34}H_{38}O_7S$
Mol. Weight: 590.23
Physical appearance: Pale yellow liquid
Yield: 85%

Monotrityl tetraethylene glycol (58 g, 132 mmol) was dissolved in THF under stirring. To the above solution, aq solution of KOH (26 g, 464 mmol) was added and allowed to stir for 10 minutes. Then, a solution of tosyl chloride (75 g, 398 mmol) in THF was slowly added and allowed to react for 12 hours at RT. Upon completion, reaction was quenched by dropwise addition of water and extracted with DCM for thrice. Combined organic layer was dried over Na$_2$SO$_4$ and concentrated under reduced pressure to get a crude product which was purified using silica gel column chromatography using EtOAc/Hexane as eluent. The product was obtained as pale yellow liquid (66 g, 112 mmol, 85%), R$_f$=0.40 in 50% EtOAc/Hexane. $^1$H NMR (400 MHz, CDCl$_3$): $\delta_H$ 7.76 (m, J=8.4 Hz, 2H), 7.47-7.45 (m, 6H), 7.34-7.18 (m, 11H), 4.11 (t, J=4.8 Hz, 2H), 3.67-3.52 (m, 12H), 3.23 (t, J=4.8 Hz, 2H), 2.39 (t, J=2.4 Hz, 1H). MALDI-TOF MS (M+K): 629.23.

Compound 14: 3,6,9,12-tetraoxapentadec-14-yn-1-ol

14

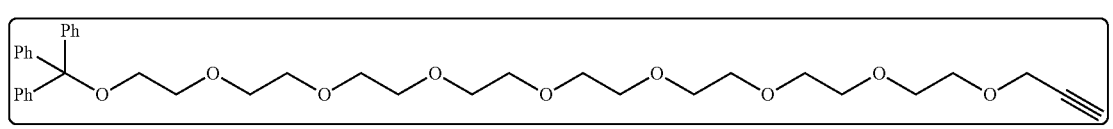

Mol. formula: $C_{11}H_{20}O_5$
Mol. Weight: 232.13
Physical appearance: pale yellow liquid
Yield 88%

In an oven dried RBF, tetraethylene glycol (15 g, 77 mmol) was dissolved with stirring in THF at 0° C. Sodium hydride (NaH) (1.23 g, 51 mmol) was added to a flask in small portions immediately. After 15 minutes, propargyl bromide (6.13 g, 51 mmol) was added drop wise, maintaining the reaction at the same temperature. Then reaction was stirred for 24 hours at RT. upon completion, excess NaH was quenched with drop wise addition of water. Resulting reaction mixture was extracted in DCM thrice. Combined organic layer was dried over Na$_2$SO$_4$ and concentrated under vacuum to get crude product which was purified using silica gel column chromatography using DCM/MeOH as eluent to get pale liquid Yield (7 g, 30 mmol, 88%), R$_f$=0.39 in 5% MeOH/DCM. $^1$H NMR (400 MHz, CDCl$_3$) $\delta_H$ 3.92 (d, J=2.4 Hz, 2H), 3.44-3.36 (m, 15H), 3.31 (t, j=4.4 Hz, 3H), 2.34. (t, d=2.4 Hz, 1H). $^{13}$C NMR (100 MHz, CDCl$_3$) $\delta_C$ 79.15, 74.46, 72.03, 69.95, 69.89, 69.86, 69.70, 69.68, 68.43, 60.82, 57.68, 53.30. HRMS (M+Na) 255.12.

Compound 15: 1,1,1-triphenyl-2,5,8,11,14,17,20,23,26-nonaoxanonacos-28-yne

15

Mol. formula: $C_{38}H_{50}O_9$
Mol. Weight: 650.35
Physical appearance: Pale yellow liquid
Yield: 71%

In an oven dried RBF, monopropargyl oligoethylene glycol (13 g, 56 mmol) and trityl tosyl tetraethylene glycol (56 g, 112 mmol) was dissolved in THF under stirring. Then, sodium hydride (NaH) (5.1 g, 224 mmol) was added in a small portion at 0° C. The reaction was allowed to react for 12 hours at RT. Upon completion, excess of NaH was quenched by dropwise addition of water, and reaction mixture was extracted with DCM for thrice. Combined organic layer was dried over sodium sulphate (NaSO$_4$) and on concentrated under reduced pressure to get the crude residue, which was purified using silica gel column chromatography using MeOH/DCM as eluent, R$_f$=0.47 in 5% MeOH/DCM. $^1$H NMR (400 MHz, CDCl$_3$): $\delta_H$ 7.47-7.45 (m, 6H), 7.31-7.20 (m, 9H), 4.20 (d, 2.4 Hz, 2H), 3.71-3.61 (m, 27H), 3.23 (t, J=4.4 Hz, 3H), 2.43 (t, J=2.4 Hz, $^{13}$C NMR (100 MHz, CDCl$_3$): 144.28, 128.87, 127.90, 127.06, 77.16, 70.94, 70.83, 70.77, 70.72, 70.67, 70.60, 70.56, 69.27, 63.48, 58.56, 53.57. MALDI-TOF MS (M+K): 689.38.

Compound 16: 3,6,9,12,15,18,21,24-octaoxaheptacos-26-yn-1-ol

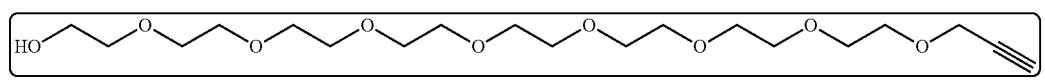

Mol. formula: C$_{19}$H$_{36}$O$_9$
Mol. Weight: 408.24
Physical appearance: Pale yellow liquid
Yield: 50%

In an oven dried RBF, mixture of monotritryl octaethylene glycol (13 g, 20 mmol) and p-toulenesulfonic acid (TsOH) (11.4 g, 60 mmol) was taken and dissolved in MeOH under stirring. The mixture was allowed to react for 12 hours at RT. Upon completion, methanol was evaporated under reduced pressure. To the obtained residue water was added and extracted thrice in DCM. Combined organic layer was dried over sodium sulphate (NaSO$_4$) and on concentrated under reduced pressure to get the crude residue, which was purified using silica gel column chromatography using MeOH/DCM as eluent, R$_f$=0.43 in 5% MeOH/DCM. $^1$H NMR (400 MHz, CDCl$_3$) $\delta_H$ 4.19 (d, J=2.4 Hz, 2H), 3.72-3.59 (m, 32H), 2.43 (t, J=2.4 Hz, 2H). $^{13}$C NMR (100 MHz, CDCl$_3$) $\delta_C$ 79.77, 74.67, 72.70, 70.72, 70.67, 70.51, 70.40, 69.22, 61.83, 58.52, 31.07. MALDI-TOF MS (M+K): 447.23.

Compound 17: 3,6,9,12,15,18,21,24-octaoxaheptacos-26-yn-1-yl 4-methylbenzenesulfonate

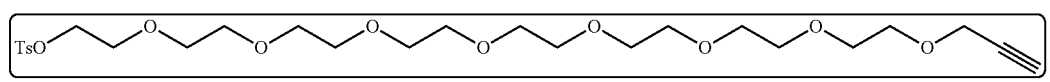

Mol. formula: C$_{26}$H$_{42}$O$_{11}$S
Mol. Weight: 562.24
Physical appearance: pale yellow liquid
Yield: 42%

In an oven dried RBF, compound 7 (4.8 g, 20 mmol) was dissolved in THF under stirring. To the above solution, aq solution of KOH (26 g, 464 mmol) was added and allowed to stir for 10 minutes. Then, a solution of tosyl chloride (75 g, 398 mmol) in THF was slowly added and allowed to react for 12 hours at RT. Upon completion, reaction was quenched by dropwise addition of water and extracted with DCM for thrice. Combined organic layer was dried over Na$_2$SO$_4$ and concentrated under reduced pressure to get a crude product which was purified using silica gel column chromatography using MeOH/DCM as eluent to get pale yellow liquid. (5 g, 9 mmol, 42%), R$_f$=0.4 in 5% methanol/DCM. $^1$H NMR (400 MHz, CDCl$_3$) $\delta_H$ 7.77 (d, J=8 Hz, 2H), 7.32 d, J=8 Hz, 2H), 4.18 (d, J=2.4 Hz, 2H), 4.14 (t, J=3.2 Hz, 2H), 3.69-3.66 (m, 6H), 3.65-3.61 (m, 20H), 3.57 (s, 4H), 2.42 (m, 4H). $^{13}$C NMR (100 MHz, CDCl$_3$) $\delta_C$ 144.78, 132.79, 129.76, 127.87, 70.60, 70.42, 69.20, 68.56, 21.56.

MALDI-ToF (M+K): 601.11.

Compound 18: 1-(3,6,9,12,15,18,21,24-octaoxaheptacos-26-yn-1-yl)piperazine the linear scale-up of the procedure mentioned above for understanding the self-assembly behavior.

Lysozyme Modification

Lysozyme was also tested using the above procedure and probe reacted successfully as shown in Scheme 11, depicted

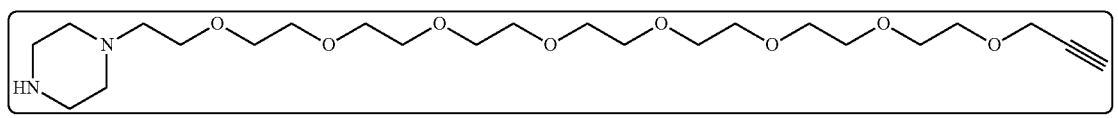

Mol. formula: $C_{23}H_{44}N_2O_8$
Mol. weight: 476.6
Physical appearance: yellow liquid
Yield: 76%

Tosylated monopropargyl OEG (compound 8) and piperazine was dissolved in THF. Then the mixture was refluxed at 61° C. After 12 hour, reaction mixture heated to evaporate THF under vacuum and the reaction mixture was re dissolved in dioxane and filtered to remove piperazine. Finally the reaction mixture was purified using column chromatography directly using 2% TEA in MeOH/DCM (5%) system.
$^1$H NMR (400 MHz, CDCl$_3$) $\square_H$ 4.20 (d, J=2.4 Hz, 2H), 3.72-3.57 (m, 32H), 2.92 (t, J=7.2 Hz, 4H), 2.58 (t, J=6.0 Hz, 2H), 2.44 (t, J=2.4 Hz, 2H). MALDI-ToF (M+K): 515.26.

Figure 9:
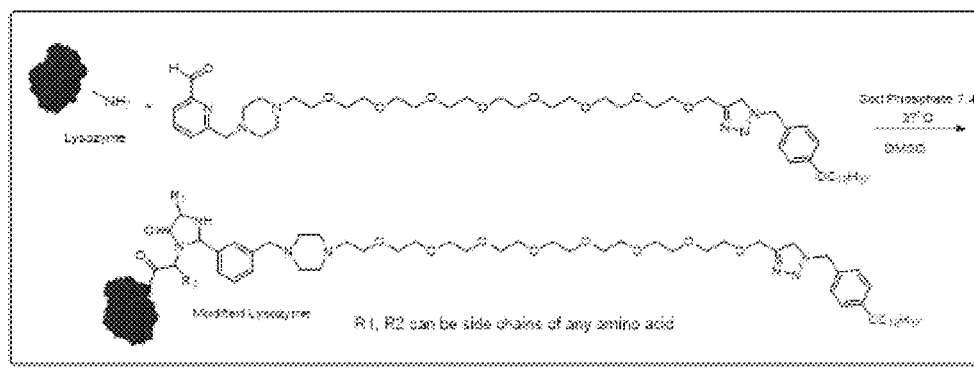
FIG. 9 shows synthesis of a modified lysozyme.
Figure 10:
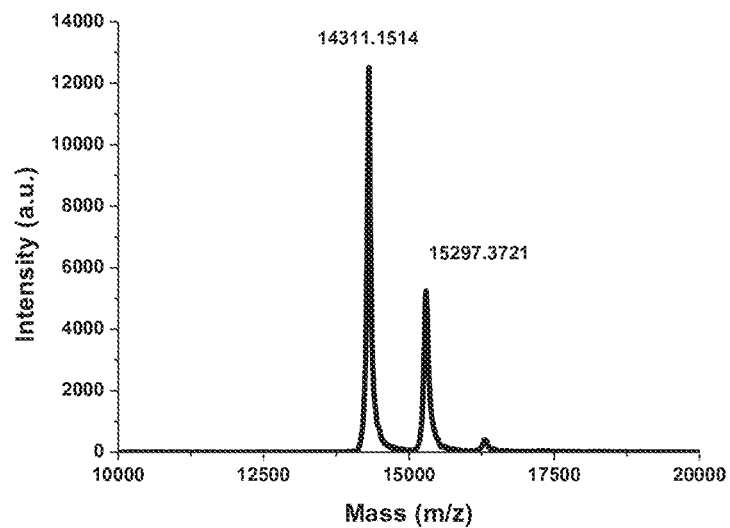
FIG. 10 depicts Maldi-TOF of N terminus modified lysozyme.

Compound 19; 6-(4-(3,6,9,12,15,18,21,24-octaoxaheptacos-26-yn-1-yl)piperazin-1-yl)methyl)picolinaldehyde in FIG. 9, and FIG. 10, depicting Maldi-TOF data of N terminus modified lysozyme. Scheme 11 shows modification of an α-amine at the N terminus of lysozyme.

Figure 11:
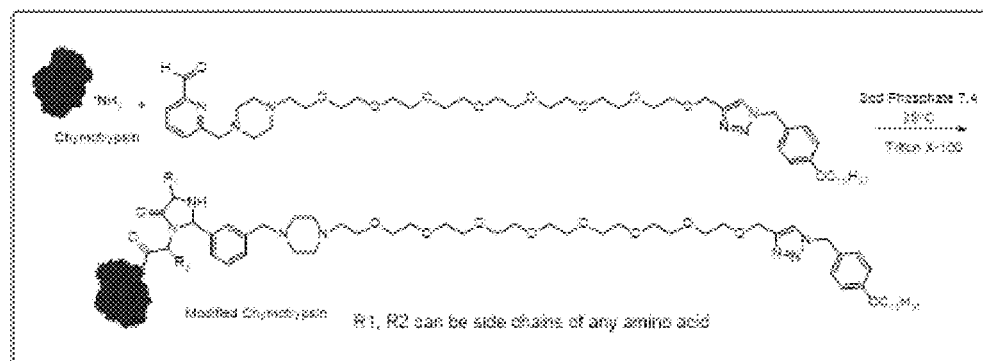
FIG. 11 shows synthesis of a modified chymotrypsin.
Figure 12:
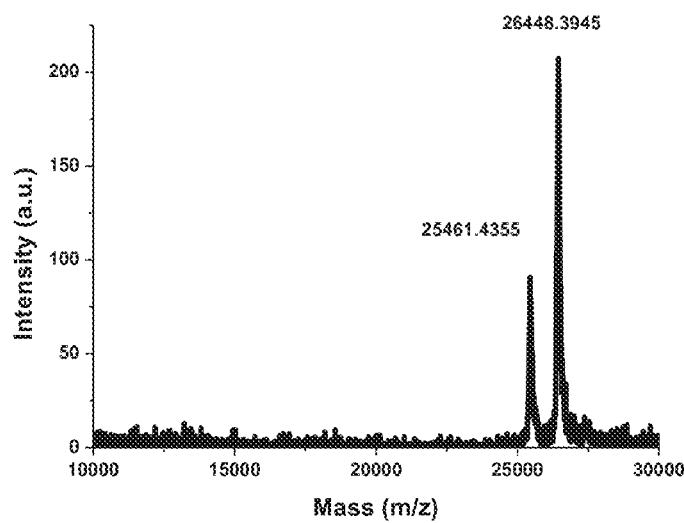
FIG. 12 depicts Maldi-TOF of N terminus modified Chymotrypsin.

Chymotrypsin Modification:

Chymotrypsin was also tested using the above procedure and probe reacted successfully as shown in Scheme 12, depicted in FIG. 11, and FIG. 12, depicting Maldi-TOF data of N terminus modified Chymotrypsin. Scheme 12 shows modification of an α-amine at the N terminus of Chymotrypsin.

Figure 13:
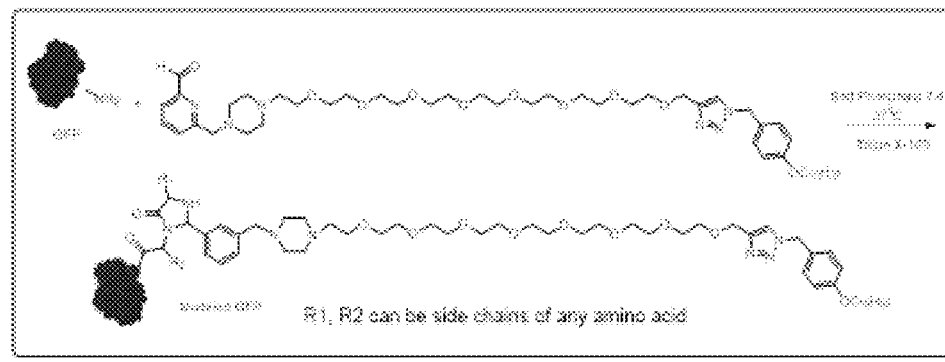
FIG. 13 shows synthesis of a modified green fluorescent protein (GFP).
Figure 14:
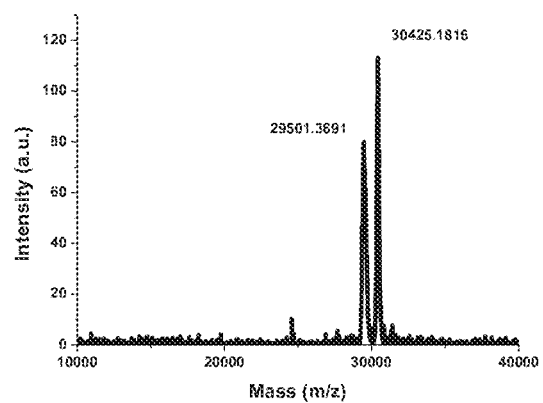
FIG. 14 depicts Maldi-TOF of N-terminus modified GFP.

Green Fluorescent Protein (GFP) Modification:

Green Fluorescent protein (GFP) may be modified as shown in Scheme 13, depicted in FIG. 13, and FIG. 14,

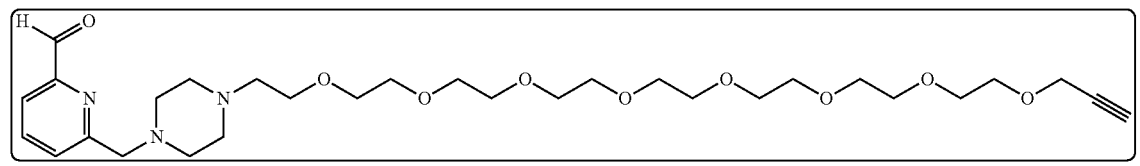

Mol. formula: $C_{30}H_{49}N_3O_9$
Mol. weight: 595.7
Physical appearance: yellow liquid
Yield: 60%

Tosylated 2-PCA and K$_2$CO$_3$ were dissolved in ACN. Then the mixture was refluxed for 12 hours. Finally the reaction mixture was purified using column chromatography directly using 2% TEA in MeOH/DCM (5%) system.
MALDI-ToF (M+K): 634.30.

Protein Modification;

Protein modification was carried out according to the previously reported protocol3. In brief, triton X-100 was used to solubilize the active amphiphilic probe (AAP) at concentrations 100 times (20 mM) more than CMC or 2% of the total volume of the reaction mixture. Typically, for test reactions, the final volume of the reaction mixture was 1 mL. Proteins were weighed in microcentrifuge tubes and 500 μL 50 mM sodium phosphate pH 7.4 was added and mixed gently with a pipette to make 200 μM solutions. Then AAPs (50 to 100 equivalents) were weighed in a different microcentrifuge tube, followed by addition of 20 μL triton X-100 and 480 μL of 50 mM sodium phosphate pH 7.4 and vortexed for 15 minutes. When the AAP solution becomes clear, the protein solution was added into AAP solution to get 100 μM (1 mL) protein solutions and allowed to react for 24 h on rotospin at 10 rpm at 25° C. Protein modifications were carried out in falcon tubes at 200 mg scale following depicting Maldi-TOF data of N terminus modified GFP. Scheme 13 shows modification of an α-amine at the N terminus of GFP.

Figure 15:
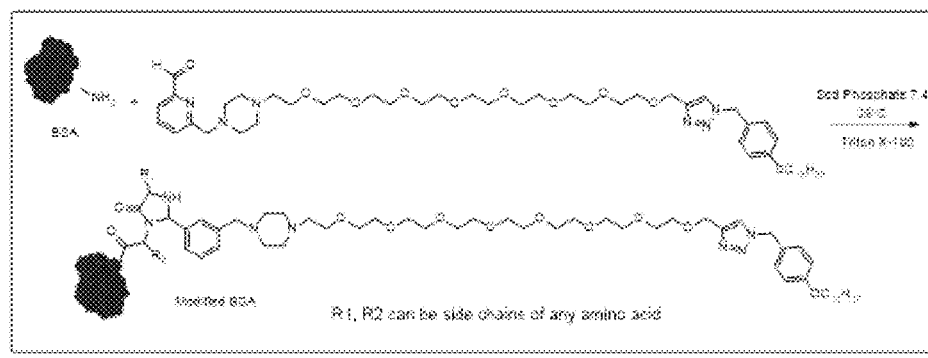
FIG. 15 shows synthesis of a modified bovine serum albumin (BSA).
Figure 16:
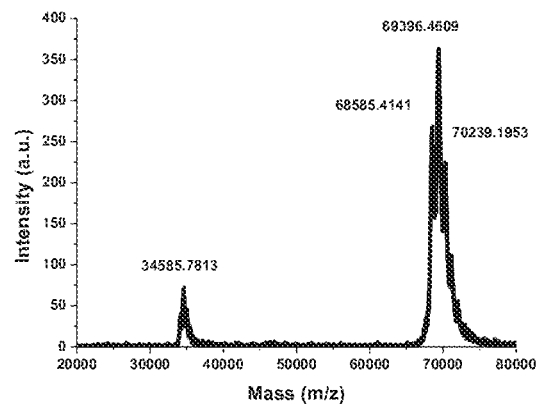
FIG. 16 depicts Maldi-TOF of N-terminus modified BSA.

BSA-Modification:

Bovine Serum Albumin (BSA) may be modified as shown in Scheme 14, depicted in FIG. 15, and FIG. 16, depicting Maldi-TOF data of N terminus modified BSA. Scheme 14 shows modification of an α-amine at the N terminus of BSA.

BSA-Thiol-Maleimide Conjugation

Figure 17:
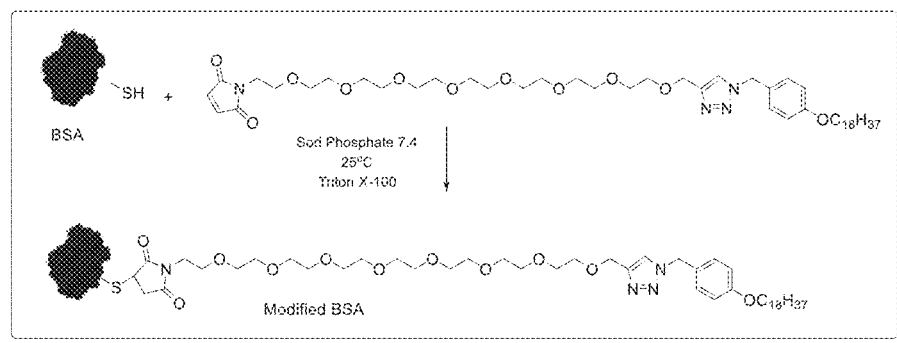
FIG. 17 shows synthesis of a thiol-modified bovine serum albumin (BSA).
Figure 18:
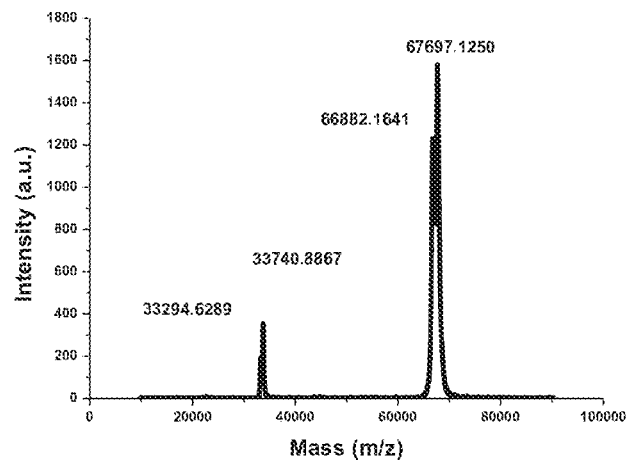
FIG. 18 depicts Maldi-TOF of Thiol modified BSA.

Bovine Serum Albumin (BSA) may be modified as shown in Scheme 15, depicted in FIG. 17, and FIG. 18, depicting Maldi-TOF data of Maldi-TOF of Thiol modified BSA. Scheme 15 shows modification of a thiol residue of BSA using a maleimide probe.

Figure 19:
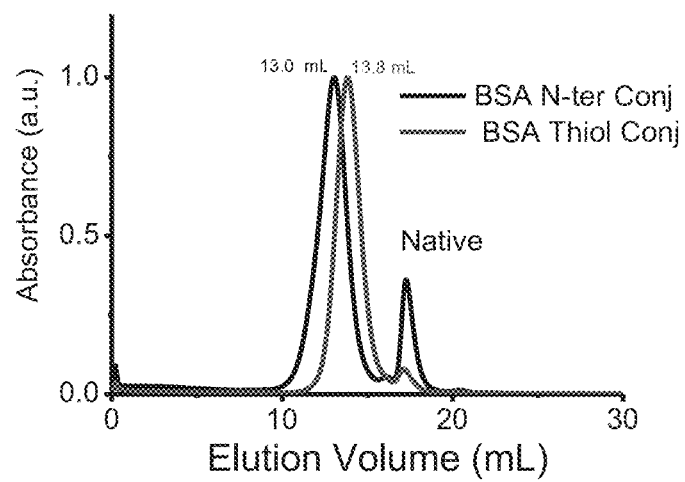
FIG. 19 shows SEC data of purified BSA thiol conjugate with respect to N-terminus conjugate.

FIG. 19 shows SEC data of purified BSA thiol conjugate with respect to N-terminus conjugate.

TABLE 1

Summary of self-assembly data

| S. No. | Protein Conjugate | Elution Vol SEC (mL) | Rel Mol Wt SEC (kDa) | Oligomeric state (mer) | $D_h$ DLS (nm) |
|---|---|---|---|---|---|
| 1 | BSA Nat | 17.4 | 66 | 1 | — |
| 2 | BSA-OEG-C18-1T | 13 | 700 | 10 | 13.24 |

TABLE 1-continued

Summary of self-assembly data

| S. No. | Protein Conjugate | Elution Vol SEC (mL) | Rel Mol Wt SEC (kDa) | Oligomeric state (mer) | $D_h$ DLS (nm) |
|---|---|---|---|---|---|
| | (N-terminus) | | | | |
| 2 | BSA-OEG-C18-1T (Thiol residue) | 13.8 | 630 | 9 | — |
| 3 | CHY Nat | 19.0 | 25 | 1 | — |
| 4 | CHY-OEG-C18-1T | 14.6 | 400 | 16 | 11.73 |
| 5 | LZ Nat | 20.9 | 14 | 1 | — |
| 6 | LZ-OEG-C18-1T | 17.9 | 50 | 3 | — |
| 7 | GFP Nat | 18.7 | 30 | 1 | — |
| 8 | GFP-OEG-C18-1T | 14 | 330 | 10 | — |

Advantages:

The present process provides for site specific modification in proteins/peptides with alpha amine of the N-terminus or free thiol residue (native or introduced at any position) of any protein/peptide as uniquely reactive site. The protein modification of the present invention is universal and hence any protein/peptide can be converted into amphiphilic proteins/peptides. The present process provides a new platform for the functionalization of 'alpha amine at the N-termini' as well as Thiol residue (Native or Introduced at any position) of any proteins/peptides which can be applied for a variety of proteins towards high biological activities.

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

REFERENCES

The following references are incorporated by reference herein.
1 Rosen, C. B. & Francis, M. B. Targeting the N terminus for site-selective protein modification. *Nature chemical biology* 13, 697 (2017).
2 MacDonald, J. I., Munch, H. K., Moore, T. & Francis, M. B. One-step site-specific modification of native proteins with 2-pyridinecarboxyaldehydes. *Nature chemical biology* 11, 326-331 (2015).
3. Sandanaraj, B., Reddy, M., Bhandari, P., Kumar, S. & Aswal, V. Rational Design of Supramolecular Dynamic Protein Assemblies Using a Micelle-Assisted Activity-based Protein Labeling Technology. *Chemistry—A European Journal* (2018).

We claim:

1. A site-modified protein/peptide amphiphile of general Formula (Ia),

MP-SG-HT (Ia)

wherein:
MP is a modified protein selected from the group consisting of a modified bovine serum albumin (BSA), a modified green fluorescent protein (GFP), a modified lysozyme, modified proteases, a modified subtilisin, a modified fusion protein, genetically edited modified proteins, modified antibodies, and modified peptides;
SG is a functionalized oligoethylene glycol hydrophilic spacer group bound to an N-terminal amino acid of the modified protein MP;
HT is a hydrophobic tail comprising a benzyl ether dendrimer with an alkyl chain;
wherein the site-modified protein/peptide amphiphile of general Formula (Ia) is a a reaction product obtained by reaction between the N-terminal amino acid of the modified protein MP and a 2-pyridine carboxaldehyde (2-PCA) compound of formula II:

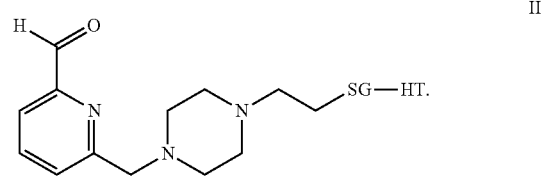

2. A site-modified protein/peptide amphiphile selected from the group consisting of:
(i) BSA conjugated at an N-terminal amino acid with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-yl)methyl) picolinaldehyde amphiphilic probe;
(ii) Chymotrypsin conjugated at an N-terminal amino acid with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-yl) methyl) picolinaldehyde amphiphilic probe;
(iii) Lysozyme conjugated at an N-terminal amino acid with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-yl) methyl) picolinaldehyde amphiphilic probe; and
(iv) GFP conjugated at an N-terminal amino acid with 2-pyridine carboxaldehyde functionalized 6-((4-(1-(1-(4-(octadecyloxy)benzyl)-1H-1,2,3-triazol-4-yl)-2,5,8,11,14,17,20,23-octaoxapentacosan-25-yl)piperazin-1-yl) methyl) picolinaldehyde amphiphilic probe.

3. A composition comprising the site-modified protein/peptide amphiphile of claim 1 and a pharmaceutical excipient.

4. A process for synthesis of the site-modified protein/peptide amphiphile of claim 1, comprising:
i. functionalizing the oligoethylene glycol hydrophilic spacer group with 2-pyridine carboxaldehyde to obtain a functionalized active amphiphilic probe (AAP), and
ii. reacting a protein or peptide with 50 to 100 equivalents of the functionalized active amphiphilic probe (AAP) of step (i) to obtain a conjugated protein or peptide with a modified N-terminal amino acid; and
iii. self-assembling the conjugated protein or peptide through micelle assisted protein labelling to yield the site-modified protein/peptide amphiphile.

* * * * *